United States Patent [19]
Ahlfors

[11] Patent Number: 5,935,805
[45] Date of Patent: Aug. 10, 1999

[54] MEASUREMENT OF BILIRUBIN ALBUMIN BINDING

[75] Inventor: Charles E. Ahlfors, San Francisco, Calif.

[73] Assignee: Research Corporation Technologies, Inc., Tucson, Ariz.

[21] Appl. No.: 08/980,267

[22] Filed: Nov. 28, 1997

Related U.S. Application Data

[63] Continuation-in-part of application No. 08/757,930, Nov. 27, 1996, Pat. No. 5,804,405.

[51] Int. Cl.[6] .............................. C12Q 1/26; C12Q 1/28; C12Q 1/00; C12Q 1/62
[52] U.S. Cl. .................................. 435/25; 435/28; 435/4; 435/10; 435/964; 436/12; 436/97
[58] Field of Search .................................. 435/25, 28, 4, 435/10, 964; 436/12, 97

[56] References Cited

U.S. PATENT DOCUMENTS 4,338,095  7/1982  Wu ............................................ 435/25

FOREIGN PATENT DOCUMENTS 0 024 112  2/1981  European Pat. Off. .

OTHER PUBLICATIONS

International Search Report of PCT Application PCT/US97/21275 (Nov. 1997).

Ahlfors, "Effect of Serum Dilution on Apparent Unbound Bilirubin Concentration as Measured by the Peroxidase Method", Clinical Chemistry, vol. 27, No. 5, 1981, pp. 692–696.

Jacobsen, et al. "Determination of Unbound Bilirubin he Serum of Newborns", Clinical Chemistry, vol. 20, No. 7, 1974, pp. 783–789.

Labrune, et al. "Gunn rats: a reproducible experimental model to compare the different methods of measurements of bilirubin serum concentration . . . ", Clinica Chimica Acta, 192, 1990, pp. 29–34.

Wells, et al. "Relationships of Bilirubin Binding Parameters", Clinical Chem, vol. 28, No. 3, 1982, pp. 432–439.

Wennberg et al, Clin. Chem., vol. 25 (8), pp. 1444–1447, (1979).

*Primary Examiner*—Louise N. Leary
*Attorney, Agent, or Firm*—Scully, Scott, Murphy & Presser

[57] ABSTRACT

The present invention is directed to the determination of unconjugated and unbound bilirubin in a sample.

21 Claims, 5 Drawing Sheets

MEASUREMENT OF BILIRUBIN ALBUMIN BINDING

RELATED APPLICATIONS

This is a continuation-in-part of application, U.S. Ser. No. 08/757,930, filed on Nov. 27, 1996 now U.S. Pat. No. 5,804,405.

FIELD OF THE INVENTION

This invention relates generally to the determination of unconjugated and unbound bilirubin in a sample. The instant invention also can be used in the diagnosis and treatment of hyperbilirubinemia.

BACKGROUND OF THE INVENTION

Bilirubin is a bile pigment which is a metabolic product of heme formed from the degradation of erythrocytes by reticuloendothelial cells. It can also be formed by the breakdown of other heme-containing proteins such as cytochromes. The most typical biological form of bilirubin is bilirubin IXa.

Bilirubin IXa normally circulates in the plasma of the bloodstream in several forms. One form has been designated as "unconjugated" or "indirect" bilirubin. The unconjugated bilirubin may complex to serum albumin and as such is designated as "bound" unconjugated bilirubin, or it may exist in a non-albumin bound or free form and as such it is designated as "unbound" unconjugated bilirubin. Both bound and unbound unconjugated bilirubin are normally transported to the liver, wherein they are taken up by the liver cells and converted to a polar conjugate form. The conversion typically involves the transfer of glucuronic acid molecules, catalyzed by the enzyme hepatic glucuronyl transferase, to the unconjugated bilirubin. This converted bilirubin is designated in the art as "conjugated" or "direct" bilirubin. Some of the conjugated bilirubin may leak back into the bloodstream. Conjugated bilirubin in the bloodstream, like unconjugated bilirubin, can bind to albumin, although the unconjugated form seems to bind to albumin more tightly. Thus, bilirubin in the blood exists in four forms: (1) bound conjugated bilirubin, (2) unbound conjugated bilirubin, (3) bound unconjugated bilirubin and (4) unbound unconjugated bilirubin. To summarize, (1) and (2) together are known as "direct" bilirubin, while (3) and (4) together are termed "indirect" bilirubin. These four fractions generally comprise the serum or plasma bilirubin concentration. However, a fifth component, delta bilirubin, has been described which is a bilirubin covalently linked to albumin. It is a very small fraction of the total bilirubin and not relevant to this discussion.

Unconjugated but not conjugated bilirubin can poison many vital cell functions, and a variety of experimental and clinical evidence suggests that unbound unconjugated bilirubin is a potential neurotoxin. Specifically, since it is not restricted by albumin binding, unbound unconjugated bilirubin can act as a neurotoxin because of its ability to migrate from the vascular space into the nervous system where it can complex with nervous tissue causing irreversible damage. Typically, unbound unconjugated bilirubin comprises less than 0.05% of the fraction of total bilirubin in the blood and is therefore difficult to measure. Disease states resulting in elevated levels of serum bilirubin may raise either "conjugated" or "unconjugated" levels of bilirubin or both forms simultaneously. However, only elevated unconjugated and unbound forms predispose a patient to neurological bilirubin toxicity.

Newborn infants suffering from high levels of unconjugated bilirubin (i.e., hyperbilirubinemia) become jaundiced after birth and are susceptible to developing kernicterus, which is an accumulation of unconjugated bilirubin in tissues of the nervous system, particularly the basal ganglia of the developing brain. This condition, also designated as bilirubin encephalopathy, may produce athetoid cerebral palsy, ocular palsy, deafness, mental retardation, and defects in fine motor control and cognitive function. Neonates afflicted with hemolysis and infants born prematurely compose the highest risk groups for bilirubin encephalopathy; however, kernicterus has also been reported in jaundiced term newborns with no clear pathological etiology for their jaundice.

Most newborns develop transient unconjugated hyperbilirubinemia in the first few days of life. There has been a recent resurgence in bilirubin encephalopathy (kernicterus) in term and near term newborns that has been attributed both to early postnatal hospital discharge and less concern about bilirubin toxicity by health care providers.

Approximately 1–2% (40,000 to 80,000) newborns per year in the United States are readmitted to the hospital for hyperbilirubinemia and about 5% (2000 to 4000 newborn) will have a total bilirubin concentration high enough to consider treatment by exchange transfusion.

Physicians faced with treatment decisions for these hyperbilirubinemic babies must determine whether the jaundice is severe enough to require exchange transfusion. Since both the exchange transfusion and jaundice are associated with significant risks to the patient, including death, the laboratory data on which these decisions are based are very important. The decision to perform exchange transfusion on a newborn is usually based on total conjugated and unconjugated blood bilirubin levels because unbound, unconjugated bilirubin is not easily measured. In fact, no routine clinical laboratory method exists for this purpose. Moreover, the concentration of total bilirubin in the blood has poor sensitivity and specificity in predicting the risk of developing kernicterus. For example, a TBC (total bound bilirubin concentration) of 15 mg/dL when used as the exchange transfusion level for term newborns with hemolysis has a sensitivity of about 83% and a specificity of about 78%. If this criterion were used for medical decision making without additional considerations, about 17% of the babies needing an exchange transfusion would not receive one and would suffer neurological injury. Furthermore, 22% of those not needing an exchange transfusion would receive one anyway along with the attendant risks. Therefore, exchange transfusion treatments may be performed needlessly upon neonates who do not need it while some requiring treatment will not receive it.

Measurement of unbound unconjugated bilirubin (neurotoxic fraction of the blood bilirubin) would be a better way to determine when a jaundiced baby needs an exchange transfusion.

Two classes of medical diagnostic tests have been used to determine the need for treatment by exchange transfusion by measuring levels of substances which are believed to correlate significantly with levels of unbound unconjugated bilirubin in the patient. These tests are based upon the following equation $$bu + bc + a \rightleftharpoons A{:}bu,bc$$

wherein bu is the unbound unconjugated bilirubin, bc is the unbound conjugated bilirubin, a is the serum unbound albumin, and A:bu,bc is the albumin complexed with unconjugated and conjugated bilirubin. Put simply, then the first method measures the unbound albumin (a), while the second method (peroxidase) measures the total amount of unbound unconjugated and unbound conjugated (i.e., bu+bc). More specifically, the first type depends upon measuring circulating levels of albumin binding sites unoccupied by bilirubin (i.e., unbound albumin) to predict the "saturation" of albumin with bilirubin. Since albumin binds with unbound unconjugated bilirubin, it has been suggested that knowledge concerning the level of unbound albumin would correlate indirectly with the amount of unbound unconjugated bilirubin in a patient. This approach assumes that albumin has one primary binding site for bilirubin and that any additional bilirubin binding sites are irrelevant. These tests attempt to determine a total bilirubin concentration at which the albumin will become "saturated" with bilirubin. If the tests determine that the amount of circulating unbound albumin is too small to bind the amount of bilirubin in the blood, exchange transfusion would be recommended. The unbound bilirubin, although not measured directly, is assumed to be proportional to the degree of albumin saturated with bilirubin. Again, when the albumin is deemed saturated with bilirubin, exchange transfusion is recommended.

Such tests, however, have unreliable endpoints and do not accurately reflect the "true" level of unbound unconjugated bilirubin in the patient because a single albumin molecule can bind more than one bilirubin molecule, and the bilirubin molecules may cause allosteric changes in the albumin making the concept of "saturation" ambiguous and the endpoint unreliable.

The second class of tests are not correlative tests, that is, they attempt to measure the actual levels of the various unbound bilirubin species in the blood. This second class of test method is preferred to tests using correlative methods since a test which directly measures the species of bilirubin in a sample typically exhibits a smaller margin of error. However, currently, such tests measure the total amount of unbound species of bilirubin (bc and bu) rather than the neurotoxic fraction of bilirubin in the blood. All bilirubin binding tests described to date do not discriminate between conjugated and unconjugated fraction of the unbound bilirubin.

Clinical laboratories in the U.S. do not routinely measure unbound unconjugated bilirubin concentrations. One non-correlative assay that is currently used in clinical laboratories measures total bilirubin concentration (TBC) in the serum/plasma, measuring the total of all four species of bilirubin (i.e., (1) bound conjugated bilirubin, (2) unbound conjugated bilirubin, (3) bound unconjugated bilirubin, and (4) unbound unconjugated bilirubin). For example, the TBC may be measured using bilirubin's light absorbing properties between 440 and 470 nm. The inherent absorption of bilirubin can be used to measure only the total bilirubin concentration because the differences in the absorption spectra of conjugated and unconjugated bilirubins are too subtle to allow discrimination between the two.

A second non-correlative test that is in clinical use measures both the total bilirubin concentration and the fraction of the total bilirubin that is conjugated. For example, one test measures the serum/plasma total and conjugated (direct) bilirubin concentration by converting bilirubin to a blue-violet colored diazo derivative which absorbs light above 500 nm. In this test, serum or plasma is combined with the diazo reagent (made by combining an organic acid like sulfanilic acid with nitrite at acid pH). Inasmuch as the conjugated bilirubin forms diazo derivatives much faster than unconjugated bilirubin, the direct bilirubin concentration which represents the concentration of conjugated bilirubin in the sample is calculated from the absorbance of light at 565 nm by the initial diazo derivatives. An accelerator such as methanol or caffeine and sodium benzoate is then added which accelerates the reaction of the unconjugated bilirubin with the diazo reagent. The total bilirubin is calculated from the final absorbance at 565 nm of all the diazo derivatives. The difference between the total and conjugated bilirubin is the concentration of unconjugated (indirect) bilirubin. However, even this combined data still does not provide the clinician with sufficient information about the unconjugated unbound bilirubin fraction of a serum plasma sample because it does not distinguish between the two types of unconjugated bilirubin, i.e., that which is bound to albumin and harmless and that which is unbound to albumin and potentially neurotoxic. Yet, it is the unbound unconjugated bilirubin, i.e., a tiny fraction of the TBC, which best assesses the risk of jaundiced newborns for developing bilirubin encapthalopathy. Knowledge of the concentration of unconjugated bilirubin which is unbound to albumin (and therefore potentially neurotoxic) is useful information.

Accordingly, a diagnostic test indicating unconjugated, unbound bilirubin would be preferred since it could specifically and accurately determine the neurotoxic fraction of total bilirubin in the blood. Knowledge of the concentration of unbound unconjugated bilirubin would be advantageous since its concentration may increase exponentially with any linear increase in the concentration of total bilirubin due to the effect of mass action on the binding of bilirubin with albumin. Therefore, an accurate measure of any change in the concentration of unbound, unconjugated bilirubin is desired because this species of bilirubin is extremely relevant in the clinical decision to administer the potential lifesaving but dangerous treatment of exchange transfusion.

A current kinetic technique for noncorrelative measurement of non-albumin bound bilirubin employs the horseradish peroxidase catalyzed oxidation of all species of bilirubin by peroxide (Jacobsen & Wennberg, *Clin. Chem.* 1974, 20(7), 783–789) (hereinafter referred to as "J & W method"). In this method, horseradish peroxidase catalyzes the oxidation of both conjugated and unconjugated bilirubin by peroxide to form products which are colorless at 460 nm. Bilirubin bound to albumin is protected from oxidation, and only unbound bilirubin is available for oxidation. Since only unbound bilirubin reacts with the peroxide, the reaction velocity of the oxidation of both conjugated and unconjugated bilirubin species is proportional to the concentration of unbound bilirubin within the sample. After measuring the first order rate constant ($K_p$) for the peroxidase catalyzed oxidation of unconjugated bilirubin by peroxide in albumin free solutions (i.e., where all the bilirubin is unbound), the concentration of unbound bilirubin is determined from the rate of oxidation in the sample. However, the peroxidase test that has been utilized heretofore has several limitations. The sample dilution required (about 40 fold) has been shown to alter binding of bilirubin as well as other ligands (See, for example, Ahlfors, *Clin. Chem.* 1981, 27, 692–696). In addition, direct (conjugated) bilirubin is non-neurotoxic, but, if present, is also oxidized by the peroxide, causing overestimation of the amount of the toxic unbound bilirubin concentration present in the sample. Moreover, the rate limiting dissociation of bilirubin from its complex with albumin during the test may lower the steady state level of the unbound bilirubin concentration sufficiently during the oxidation to cause significant underestimation of the unbound unconjugated bilirubin in the sample. Therefore, the unbound bilirubin measured by this method does not provide adequate information about the unbound, unconjugated bilirubin, i.e., the neurotoxic fraction (bu).

Therefore, a method which determines the concentration of unbound, unconjugated bilirubin (bu) would be greatly advantageous. The present inventor has developed such a method.

SUMMARY OF THE INVENTION

The present invention is directed to the process for determining the concentration of unbound, unconjugated bilirubin in a sample comprising:

(a) determining the concentration of conjugated "direct" and unconjugated "indirect" bilirubin in a first aliquot of said sample, (b) mixing a second aliquot of said sample with a bilirubin oxidizing reagent, and a catalytically effective amount of a standardized catalyzing reagent, in which a first order rate constant for catalyzing the oxidation of bilirubin by said oxidizing reagent has been predetermined, under conditions effective to oxidize the unconjugated bilirubin for a predetermined amount of time sufficiently short so that the amount of bilirubin oxidized is less than about 50% of the total bilirubin concentration, said dilution of said second aliquot sample from the addition of the oxidizing reagent and the catalyzing reagent being less than about 3:1 by volume, (c) stopping the oxidation reaction at said predetermined time and determining the concentration of conjugated and unconjugated bilirubin remaining in said second aliquot after oxidation, and (d) determining the steady state unconjugated unbound bilirubin concentration, designated as $b_{ss}$, from the calculation of the following equation:

$$b_{ss} = -B_o \cdot \text{Log}\, (B_t/B_o)/(\text{dilution} \cdot K_p \cdot P \cdot t) \qquad \text{EQ. 1}$$

wherein $b_{ss}$ is the steady state unconjugated unbound concentration of bilirubin;

$B_o$ is the unconjugated bilirubin concentration in said sample, its value determined in step (a);

$B_t$ is the unconjugated bilirubin concentration in said sample remaining after oxidation of bilirubin by the oxidizing reagent in the presence of standardized catalyzing reagent for a predetermined amount of time, its value determined in step (c);

dilution is the sample dilution resulting from the addition of oxidizing and catalyzing reagents to the sample;

t is the predetermined reaction time for the oxidation reaction;

P is the concentration of the catalyzing reagent; and $K_p$ is the first order rate constant for the catalyzed oxidation of bilirubin by said oxidizing reagent in the absence of albumin or other molecules capable of binding to bilirubin.

Another aspect of the present invention is directed to the process for determining the concentration of unbound, unconjugated bilirubin in a sample, when correction for background oxidation of unbound bilirubin is desired, comprising:

(a) determining the concentration of conjugated "direct" and unconjugated, "indirect" bilirubin $B_o$ in said sample as described hereinabove;

(b) mixing a second aliquot of said sample with a bilirubin oxidizing reagent, and a catalytically effective amount of a standardized catalyzing reagent, in which the first order rate constant for catalyzing the oxidation of bilirubin by said oxidizing reagent has been predetermined, under conditions effective to oxidize the bilirubin for a predetermined amount of time sufficiently short so that the amount of bilirubin oxidized is less than about 50% of the total bilirubin concentration, said dilution of said aliquot sample from the addition of said oxidizing and catalyzing reagents being less than about 3:1 by volume;

(c) stopping the oxidation reaction at said predetermined time and determining the concentration of unoxidized conjugated and unconjugated bilirubin in said second aliquot sample ($B_t$);

(d) mixing a third aliquot of said sample of equal volume to that in step (b), with an oxidizing reagent and a buffer in the absence of any added catalyzing reagent for the same amount of time as in step (b), and determining the concentration of unoxidized unconjugated bilirubin in said third aliquot ($B_b$), whereby the amount of buffer added is equal in volume to the amount of catalyzing reagent added in step (b) and the volume and concentration of oxidizing agent added is equal to that utilized in step (b); and (e) determining the steady state unconjugated non-albumin bound bilirubin concentration designated as $b_{ss}$ from the calculation of the following equation $$b_{ss} = -[B_o \cdot \text{Log}\, ((B_o - B_b + B_t)/Bo)]/(\text{dilution} \cdot K_p \cdot P \cdot t) \qquad \text{EQ. 2}$$

wherein $b_{ss}$, $B_o$, $B_t$, dilution, $K_p$, P and t are defined as above, and $B_b$ is the unconjugated bilirubin in said sample after any oxidation, in the absence of added catalyzing reagent, its value determined in step (d).

DETAILED DESCRIPTION OF THE INVENTION

Figure 1:
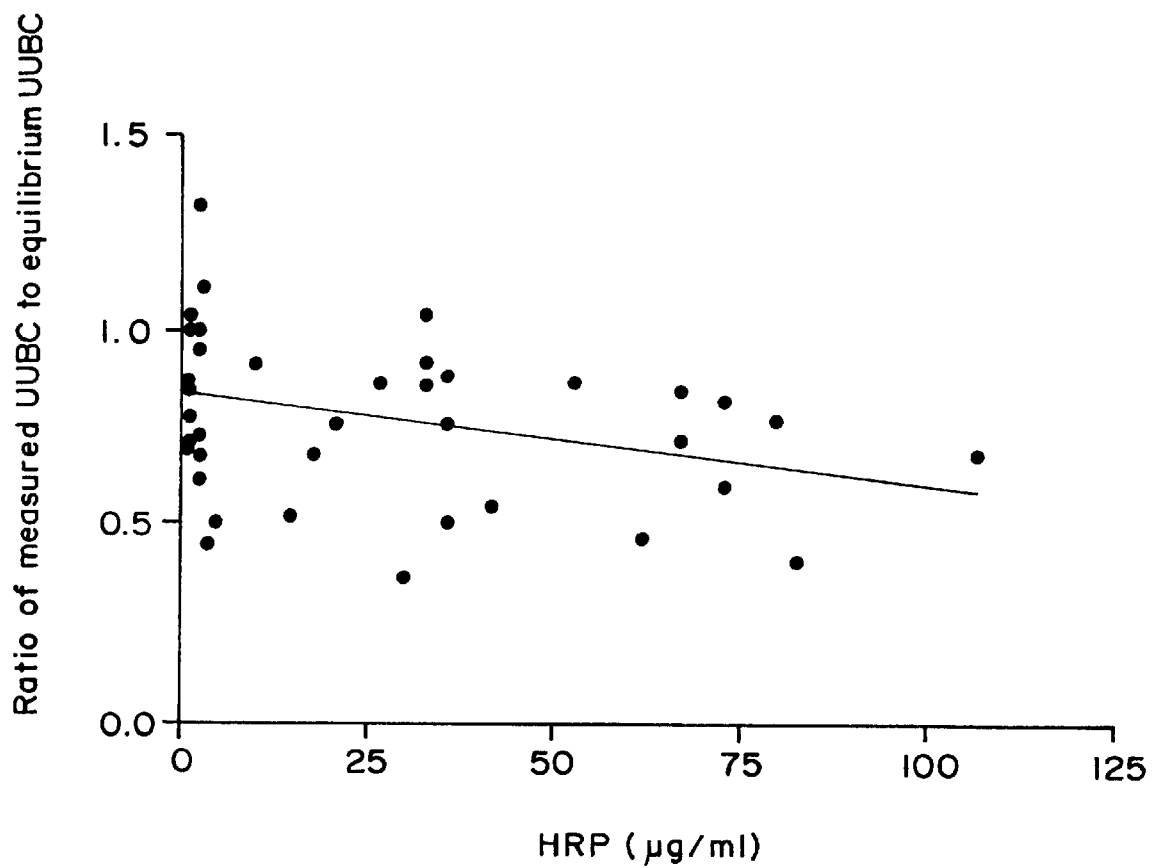
FIG. 1 depicts graphically the ratios of the measured (bss) and equilibrium unbound unconjugated bilirubin concentrations (UUBCs) obtained from 20 newborns as a function of the concentration of the catalyzing reagent, horseradish peroxidase (HRP). The decreasing slope indicates a decreasing ratio with increasing HRP concentration.

The present invention is directed to a method of determining the unconjugated unbound bilirubin concentration in a sample.

As used herein, the term "sample" refers to a fluid collected from a mammal, which normally contains bilirubin and albumin. The fluid includes, but is not limited to, bilirubin containing blood serum or plasma, cerebrospinal fluid, amniotic fluid, lymphatic fluid, and the like. The preferred fluid sample is blood serum or plasma. The biological fluid to be assayed is obtained from mammals, such as dogs, cats, mice, rats, horses, ungulates and especially humans. The most preferred fluids is a blood serum or blood plasma from a human.

The term "conjugated" as used herein refers to the biological form of bilirubin IXa after transformation in the liver where it is converted to a polar conjugate form such as, but not limited to, a water-soluble bilirubin diglucuronide.

"Unconjugated" as used herein refers to the lipid soluble form of bilirubin designated as the isoform bilirubin IXa.

As used herein, the term "bound" refers to the form of bilirubin, either conjugated or unconjugated, which is complexed with albumin.

The term "unbound" as used herein refers to the form of bilirubin, either conjugated or unconjugated, which is not complexed with or bound to albumin.

A bilirubin oxidizing agent is an oxidizing reagent which is capable of oxidizing unbound bilirubin but cannot oxidize bound bilirubin. Examples include peroxides, ferricyanides, especially ferricyanide salts, including metal salts including Group IA metal salts (e.g., potassium ferricyanide) and the like. The oxidizing agent may be organic or inorganic. The preferred oxidizing agent is a peroxide of the formula $ROOR_1$;

wherein R and $R_1$ are preferably hydrogen, or an organic hydrocarbyl moiety containing 1–6 carbon atoms. It is preferred that $R_1$ is hydrogen. The preferred peroxides are those that are commercially available and include such examples as hydrogen peroxide, t-butyl peroxide, ethyl hydrogen peroxide, and the like. However, one of ordinary skill in the art will recognize that other acceptable peroxides can also be utilized.

By "hydrocarbyl", it is meant an organic radical containing only carbon and hydrogen and containing 1–6 carbon atoms, and preferably, 1–4 carbon atoms. They may be branched or straight chained. The preferred hydrocarbyl groups are alkyl groups, such as methyl, ethyl, propyl, isopropyl, butyl, sec-butyl, isobutyl, t-butyl, pentyl, isopentyl, neopentyl, hexyl and the like.

The term "bilirubin catalyzing reagent" as used herein, refers to a composition which facilitates the oxidation of unbound but not bound bilirubin. In a preferred embodiment, such a bilirubin catalyzing reagent is a peroxidase. However, any catalyzing reagent which facilitates the oxidation of unbound bilirubin but not the oxidation of bound bilirubin can be used, such as oxygen and bilirubin oxidase which catalyzes oxidation of bilirubin by oxygen, and the like.

The term "peroxidase" refers to an enzyme that catalyzes a reaction in which a peroxide is an electron acceptor. Peroxidases have been isolated from animal and mostly plant sources by techniques known to the skilled artisan. Peroxidases are also commercially available. All of these peroxidases are contemplated by the present invention. The preferred peroxidase is horseradish peroxidase.

The term "buffer" used herein refers to any of the solutions described by Goode in Biochemistry 1996, 5, 467. Preferred buffers include phosphate buffers, such as Sorensen's phosphate buffer, especially at concentrations of 0.03–0.75M, and even more preferred at about 0.055M, at about physiological pH, e.g., at pH 7.4.

By diazo reagent, it is meant any group which will react with bilirubin and form a diazo derivative thereof. By diazo, it is meant that the compound contains the radical N=N. Virtually any diazotized aromatic amine can be used as an azo reagent in the calorimetric technique of the present method as long as the conditions taught herein have been met. Preferably, the diazo reagent, e.g., the diazotized aromatic amine utilized in this invention, is formed in situ, such as, for example, by reaction of sulfanilic acid containing a strong acid, e.g., HCl with sodium nitrite. Methods for forming diazo derivatives of the aromatic amines are well known to the skilled artisan. See, e.g., Henry, et al, Clinical Chemistry, Principles and Techniques, 2d Ed. Harper and Row, New York, N.Y. (1974), pp. 1037–1079, the contents of which are incorporated herein by reference. See also, e.g., Lillie, H. J. Conn's Biological Stains, Williams and Wilkins Company, Baltimore, Ma. (1969), Ed. VI. In general, the reaction involves the reaction of an hydrocarbyl, e.g., alkyl and especially aromatic amine with nitrous acid which is prepared in situ from the reaction of sodium nitrite and inorganic acid such as hydrochloric acid or sulfuric acid, and the like.

By aromatic, it is meant an aromatic compound wherein the number of carbon ring atoms is equal to 4n+2, wherein n is at least one. It is preferred that n is 1–10 and more preferably n is 1–5, and most preferably n is 1–3. The aromatic ring is substituted with amine and may be further unsubstituted or substituted with substituents inert to the oxidizing reagent utilized, the catalyzing reagent or the product of the oxidation of bilirubin. These additional substituents include such groups as halo, oxo, carboxy, carbalkoxy groups containing 1–6 carbon atoms, alkyl groups containing 1–6 carbon atoms, nitro groups, sulfonic acid groups, and the like. However, the aromatic amine that is utilized is preferably a primary amine. The aromatic amines used in this test are those which are commercially available and are known and/or synthesized in the laboratory by known techniques. Examples include sulfanilic acid, O-dianisidine, p-chloroaniline, 1,5-dichloroaniline, 2,4-dichloroaniline, 2-methoxy-4-nitroaniline, 1-amino anthraquinone, p-nitroaniline, 4-chloromethylaniline, 4-chloroaniline, and the like. Those of ordinary skill in the art will be aware of other aromatic amines which can form diazo reagents in situ and which are capable of being used in the calorimetric portion of the instant invention.

In a preferred method of preparing the diazo reagent, the aromatic amine is mixed with a strong acid, such as concentrated hydrochloric acid, concentrated sulfuric acid, concentrated phosphoric acid and the like which is then diluted with water, preferably distilled water and more preferably deionized water. After the addition of the water thereto, it is preferred that the concentration of the aromatic compound ranges from about 0.05M to about 1 molar, and more preferably from about 0.05M to about 0.5M. In addition, the concentration of the acid preferably ranges from about 0.05M to about 1 molar and more preferably from 0.05M to about 0.5M. To form the diazo reagent, the solution containing the aromatic amine is reacted with a solution containing a nitrite salt, e.g., a Group IA metal salt solution such as sodium nitrite, potassium nitrite, lithium nitrite, and the like. It is preferred that the molarity of the nitrite solution ranges from about 0.05M to about 1M and more preferably from about 0.05M to about 0.5 molar.

In forming the diazo reagent, it is preferred that approximately an equal amount (in moles) of the acidic nitrate solution is reacted with an equal amount (in moles) of the aromatic amine solution, although the molar ratio may range from about 4:1 to about 1:4. It is preferred that the concentration of the diazo reagent ranges from about 0.05M to about 1M and more preferably from about 0.1M to about 0.5M. Since the diazo reagent is fairly reactive, it is preferred that it is freshly prepared before use. Alternatively the diazo reagent can be prepared by mixing in one vessel the acids, the aromatic amine and the nitrite in the amounts described hereinabove to provide the desired concentration of diazo reagent.

The instant invention is useful in that it accurately measures the concentration of unbound, unconjugated bilirubin in a sample. Moreover, the instant technology determines the concentration of unbound unconjugated bilirubin in small samples with little dilution of the sample size. As noted hereinabove, the large dilution of a sample to perform the oxidation reaction promotes distortion resulting in inaccurate measurements of unbound bilirubin. The instant invention alleviates the necessity for large dilutions. Additionally, the instant invention employs colorimetric and kinetic enzymatic reactions which are readily adaptable to clinical laboratories. The present invention is inexpensive and does not require the purchase of expensive and sophisticated equipment.

As indicated hereinabove, an aspect of the instant invention is directed to a method which directly determines the concentration of the potentially neurotoxic components of total bilirubin present in a sample—i.e., unbound, unconjugated bilirubin. This method overcomes limitations imposed by large sample volumes or large dilutions, costly equipment or training, and extended processing delays. The method is inexpensive, fast, and accurate and can be performed on standard clinical laboratory instruments presently capable of measuring direct and indirect bilirubin concentrations.

There are several advantages of the instant method: (1) Combining calorimetric and kinetic (i.e., enzymatic) techniques in a single method thus permitting a direct integrated method for determining the concentration of unbound, unconjugated bilirubin in a sample; (2) small sample volumes (e.g., 100 μl or less) thus avoiding larger sample volumes which can be a limiting factor when performing laboratory tests on newborns; (3) small sample dilutions (e.g., 1:3 or less), thus avoiding any intrinsic alteration of bilirubin-albumin binding or masking effect of weakly binding drugs or endogenous bilirubin binding competitors in samples using large dilutions (i.e., in the range of about 1:40). Sample dilutions in the range of about 1:40 may alter bilirubin-albumin binding especially if weak bilirubin binding competitors are present in the sample. The masking effect due to large sample dilutions can ultimately lead to an underestimation of the concentration of unbound unconjugated bilirubin i.e., the toxic fraction of bilirubin; (4) the instant method measures unbound, unconjugated bilirubin directly instead of measuring the "saturation" of albumin with bilirubin by measuring the unoccupied bilirubin binding sites on the albumin molecule. The instant method of determining the concentrations of species of bilirubin does not lead to nonspecific endpoints in measurement because the instant methods do not assume that albumin binds a single bilirubin molecule but the instant methods take into consideration that albumin is capable of binding several bilirubin molecules; (5) the instant invention determines each species of the fraction of bilirubin which makes up the total concentration of bilirubin in a sample, thus, permitting establishment of accurate standardized reference values or permitting a strategy for establishing reference values useful during clinical treatment of bilirubin disease states; (6) the instant invention can include control reaction conditions that correct for endogenous oxidation of bilirubin in the sample in the absence of added catalyzing reagents; (7) the instant invention uses reaction conditions that eliminate or correct for the potential rate limiting dissociation of bilirubin from albumin since, if the rate of dissociation of bilirubin from its complex with albumin is the rate limiting step in the oxidation of bilirubin, the unbound bilirubin concentration can be significantly underestimated; (8) the instant invention corrects for any errors in measurement due to the oxidation of conjugated bilirubin in the sample as opposed to measuring both conjugated and unconjugated unbound bilirubin since both species can be oxidized yet only the unconjugated unbound is potentially toxic. Therefore, the conflating effect of measurements of the oxidation of both conjugated and unconjugated bilirubin can be eliminated by the present technology; (9) the instant invention eliminates error caused by interference from conjugated bilirubin which can lead to an overestimation of the unbound unconjugated bilirubin concentration; (10) expensive equipment is not required nor is time-consuming data processing; (11) technicians may be easily trained or instructed in performing the instant methods instead of requiring dedicated technician support and instrumentation to monitor change in light absorption of bilirubin over periods of time.

Additionally, a kit composed of the reagents necessary for this method can be created from stable and inexpensive reagents. After using the instant methods, reference values for levels of bilirubin can be established and employed as an adjunct in clinical treatment decisions.

The assay method of the instant invention can provide several different bilirubin assay values. For example, this method can directly determine the presence and/or concentration of unconjugated bilirubin, or the presence and/or concentration of conjugated bilirubin, or the presence and/or concentration of unconjugated unbound bilirubin, or the presence and/or concentration of bound bilirubin, or the presence and/or concentration of each of the four possible combinations of conjugated or unconjugated bilirubin which is either bound or unbound to albumin and the method can also determine the presence and/or concentration of total bilirubin which is equal to the sum of the amounts unconjugated and conjugated bilirubin. The method of the instant invention uniquely combines certain elements of both colorimetric techniques for measuring conjugated and unconjugated bilirubin with kinetic techniques for measuring unbound bilirubin.

One of the steps in the instant invention is the calorimetric method, while another step is a combination colorimetric/kinetic method step. Although illustrated hereinbelow in a particular order, the present invention is not so limiting and these steps can be performed in any order. For example, the calorimetric steps may be performed before or after the colorimetric/kinetic step as defined hereinbelow.

In performing the assay of the instant invention, the sample is obtained from a patient using standard techniques known in the art. As defined hereinabove, it is preferred that the sample is human blood serum or plasma. It is more preferred that freshly prepared serum or plasma is utilized and is preferably prepared on the day the assay is run. In addition, it is also preferred that the plasma or serum is protected from light and/or stored in the dark when not utilized. Without wishing to be bound, it is believed that these precautions prevent decreased values due to spontaneous photo-oxidation of the bilirubin component of the sample if exposed excessively to light.

In performing the assay, only a small amount of sample is required for each step. It is preferred that less than 100 $\mu$l of sample is used, and more preferably less than 80 $\mu$l and most preferably less than 75 $\mu$l of sample is utilized in total. In fact, as little as 10–15 $\mu$l of sample may be utilized in each step of the assay.

MEASUREMENT OF Bo

In looking at Equation 1 described hereinabove, one of the variables required to be determined is the concentration of unconjugated bilirubin in the sample. This indirect bilirubin is determined from the measurements of the total bilirubin in the sample and the conjugated bilirubin in the sample, as described below.

A number of standard methods of assaying or quantitatively measuring bilirubin in the art are based upon calorimetric methods, which is either measuring the inherent absorbance of the bilirubin pigment itself or by mixing bilirubin in the presence of certain reagents to form a colored reaction product which is then subjected to spectral analysis. Typically, only the total amount of bilirubin present can be determined from measuring the absorbance of the bilirubin pigment itself because the differences in the absorbance spectra of conjugated and unconjugated bilirubin are too subtle to differentiate. Therefore, many calorimetric assays for bilirubin commonly use diazotized sulfanilic acid or other diazotized reagents to form colored azobilirubin reaction products. See, for example, Malloy-Evelyn, *J. Biol. Chem.*, 119 (1937); Jendrassik-Grof, *Biochem. Z.*, 297, 81 (1938) and Walters and Gerarde, *Microchem. J.*, 15, 231 (1970), the contents of all of which are incorporated by reference.

In the diazo method, both the concentration of conjugated and unconjugated bilirubin are determined. The underlying basis for the diazo method is premised upon the faster reactivity of the conjugated bilirubin with a diazo reagent, relative to the unconjugated bilirubin, and the absorbance of light by the colored diazo derivative at about 565 nm.

An excess amount (in moles) of diazo reagent is added to an aliquot of sample. Sufficient amount of diazo reagent is added under conditions effective to react with the bilirubin in the sample. It is preferred that the amount of diazo reagent added ranges from about 20 volumes to about 10 volumes of diazo reagent for every volume of sample. In this step, as indicated hereinabove, the diazo reagent is selectively reacted with the conjugated bilirubin but does not react to any extent with the unconjugated bilirubin. The reaction is effected for sufficient time and under conditions effective for the diazo reagent to react with the conjugated bilirubin. The solution will become colored as the diazo reagent is diazotizing the conjugated bilirubin. After sufficient time for the diazo reagent to react with the conjugated bilirubin in the sample to form the diazotized derivative, preferably within about 1 min., the amount of conjugated bilirubin present is determined by spectral analysis.

The method of spectral analysis of the instant invention is carried out using any method known in the art, such as by using absorption photometry, e.g., calorimetric detection, or emission photometry, e.g., fluorimetric detection, as an appropriate mode of radiometric detection. The radiometric detection of the absorption or emission bands characteristic of the bilirubin or its diazo derivatives can be carried out using any of a variety of well known absorption or emission detection devices and techniques commonly referred to herein as a spectral analyzer. By "spectral analyzer," it is meant any method or apparatus of measuring the absorbance of a sample, such as, but not restricted to, a spectrophotometer. The detection of these spectral bands can be carried out at a predetermined time after the sample is processed so that the resultant spectral data can be readily correlated to, for example, a calibration curve based on the spectral data obtained from a series of controls containing known amounts of conjugated and unconjugated bilirubin or its diazo derivatives as determined at the same or at a different time interval. Additionally, to avoid spectral interference from potential interferents which may be present in the assay sample (e.g., hemoglobin) any of the noted absorption maxima referred to herein can be detected "off-peak." By the term "off-peak", is meant that generally spectral detection can be carried out at wavelengths about up to 20 nm from the maxima values referred to herein. Thus, as used herein, detecting a wavelength "at or near" an absorption maximum signifies at the peak wavelength ±20 nm and at an intensity no less than 50% of peak intensity.

It is preferred that the amount of conjugated bilirubin present is determined by calorimetric techniques. By calorimetric techniques it is meant that a colored reaction product is formed as a result of a chemical reaction and has unique absorption or emission characteristics measured by spectral analysis, e.g., spectrophotometer.

In the present system, the diazotized bilirubin, whether derived from conjugated or non-conjugated bilirubin, forms a colored solution. The amount of diazotized bilirubin present is measured from the absorption thereof of the diazotized derivative at a wavelength of preferably about 565 nm. However, this absorbance can be converted to amounts per volume (e.g., m grams/dL or moles/L) of conjugated bilirubin by techniques known in the art such as from a standard curve prepared from known amounts of bilirubin.

In the instant assay, this first absorbance reading provides the amount of conjugated (direct) bilirubin present in the sample. In order to determine the total amount of bilirubin present, an accelerator is added. An accelerator is a reagent which accelerates the reaction of the unconjugated bilirubin with the diazo reagent. Various accelerators, sometimes known as "effectors" or "promoters" as discussed by Herry, et al. in Clinical Chemistry Principles and Techniques, 2d Ed., Harper and Row, New York, N.Y., (1974), are known in the art for their use in bilirubin assays and include reagents such as methanol, caffeine, sodium benzoate, surfactants, bile salts, gum arabic, salicylate, and the like. It is preferred that the accelerators utilized are substantially pure. It is also preferred that they be dissolved in or mixed with water, especially distilled and/or deionized water, before being added to the sample. Sufficient accelerator is added to permit the diazo reagent to react with the remaining undiazotized, unconjugated bilirubin. It is preferred that an equal molar amount of accelerator to that of the diazo reagent added in the previous step is added to the sample containing the diazotized conjugated bilirubin.

At this point, following addition of the accelerator, the sample contains conjugated diazotized bilirubin and unconjugated diazotized bilirubin. By utilizing spectral analyses, as defined herein, the total amount of bilirubin present in the sample can be determined. It is preferred that the absorbance thereof is determined by calorimetric techniques, the absorbance value is read at about 565 nm. and the amount of total bilirubin present is determined by techniques known in the art, such as from a standard curve, from known amounts of bilirubin, which correlates absorbances with known amounts of diazotized bilirubin. The unconjugated (indirect) bilirubin is then calculated as the difference between the value of the total bilirubin and the conjugated (direct) bilirubin.

To aid in maintaining the pH within the stated range, these bilirubin determinations can be carried out in the presence of a buffer. Various buffers may be employed in using the methods of the instant invention such as those described by Good in Biochemistry, 5, 467 (1996). However, one of ordinary skill in the art can vary the pH and temperature herein to values above or below the stated ranges depending upon the particular conditions, provided that one does not use a pH or temperature which causes undesired side reactions or significant degradation of any bilirubin composition.

It will be appreciated by those of ordinary skill in the art that other reagents which function in an acceptable manner may be substituted for those described herein. For example, other buffers may be employed if they provide the desired pH range.

MEASUREMENT OF Bt

Referring back to Equations 1 or 2, this step of the instant invention operates by measuring the concentrations of $B_t$, as defined herein. $B_o$ is measured in a first aliquot of the sample by the diazo method, as described above, while $B_t$, the unconjugated bilirubin remaining after oxidation of some of the bilirubin in a second aliquot of sample, is detected by the diazo method following said oxidation.

Both conjugated and unconjugated bilirubin are oxidized by oxidizing reagents (e.g., peroxide) in the presence of a catalyzing reagent (e.g., a peroxidase) or by other oxidizing agents, such as ferricyanide to produce products identified as diazo negative reaction products, i.e., reaction products that are not diazotized, do not absorb light in the spectral region where native bilirubin absorbs light and do not form diazotized derivatives when reacted with diazo reagents. On the other hand, albumin binding of bilirubin prevents the oxidation of bilirubin so that only unbound bilirubin can be oxidized. Since as noted hereinabove, the initial rate of oxidation of unbound bilirubin is proportional to the total amount of unbound bilirubin in the sample, measurement of the unconjugated bilirubin remaining after oxidation can provide a measure of oxidation rate and thereby the concentration of unconjugated unbound bilirubin originally in the sample ($b_{ss}$; See Eq. 1). Since the oxidized products, oxidizing reagent and catalyzing reagent do not react with diazo reagents, the amounts of unoxidized bilirubin remaining after the oxidation reaction can be determined though the colorimetric technique portion of the method. As described hereinbelow, the oxidation reaction is conducted for a predetermined incubation amount of time, and then it is terminated. To determine the amount of unoxidized unconjugated bilirubin ($B_t$) remaining in the sample, after a predetermined time of oxidation, the colorimetric technique is used. The beauty of this technique is that the reagent used in the colorimetric technique also denatures the bilirubin catalyzing reagent, e.g., the peroxidase, such as horseradish peroxidase, thereby stopping the enzymatic reaction. For example, diazo reactions are typically carried out in the range of about between pH 1 and pH 2 to enhance the absorbance of the derivatives. At such a range of pH, peroxidases, which are utilized in the oxidation step, e.g, horseradish peroxidase, and which catalyze the oxidation reaction of unbound species of bilirubin, are denatured. As noted hereinabove, bilirubin oxidation products, peroxides, and peroxidases do not react with diazo reagents. Therefore, if bilirubin in a sample is oxidized for a given time following which a diazo reagent is added, the oxidation reaction is terminated, and the remaining concentration of total and conjugated bilirubin can be measured. If the concentration of total and conjugated bilirubin are determined before and a set time after the initiation of the oxidation of bilirubin in the sample, these measurements can be subsequently used to calculate the concentration of unbound, unconjugated bilirubin, using EQS 1 or 2, and as described hereinbelow.

Thus, the addition of the acidic diazo reagent or other calorimetric agent immediately denatures the enzyme so that the oxidation reaction is immediately terminated by its addition and permits the calculation of the unbound unconjugated bilirubin concentration.

In the description of the measurement of $B_t$ hereinabove, it is important that the sample remains in the critical pH range. It is preferred that a buffer is utilized so that the pH of the sample remains within a predetermined pH in which the catalyzing reagent is effective during the oxidation. Preferably, the pH of the sample is maintained at a pH ranging from about 7.2 to about 7.6 and especially at about 7.4. Any buffer normally used by the skilled artisan to maintain the pH in this range may be utilized, but it is preferred that a phosphate buffer, and more specifically, a dihydrogen phosphate buffer is utilized. Sufficient amount of buffer is added to maintain the sample solution at this pH range. The bilirubin catalyzing reagent, e.g., peroxidase, and the bilirubin oxidizing reagent, e.g., peroxide are prepared in this buffer, so that no additional buffer is required to be added. The reagents added to the sample to promote the oxidation may be present in the buffer so that the sample dilution is minimized. In the method of the present invention, up to four aliquots of sample may be required. However, as described hereinbelow, embodiments of the present invention require one, two or three aliquots of sample, depending upon the approximations utilized and depending upon circumstances, as described below.

The $B_o$ concentration of the unconjugated bilirubin in an aliquot of a sample is determined by the calorimetric (e.g. diazo) technique as described hereinabove and before any oxidation takes place. This determination utilizes a first aliquot of sample.

The oxidizing reagent and the catalyzing reagent are added to a second aliquot of sample. The oxidizing reagent is preferably mixed with buffer and is added to the aliquot sample in sufficient amounts to oxidize the bilirubin present in the sample, in the presence of the catalyzing reagent, which is also preferably mixed with buffer. If additional buffer is required to bring the pH to the appropriate value, additional buffer may be added. The amount of bilirubin present is determined after a specified time for oxidation from the calorimetric analysis described hereinabove. Preferably, the oxidizing reagent solution is sufficiently concentrated so that a minimal volume thereof is added to the sample. For example, it is preferred that approximately about 0.1 volumes to about 1 volume of oxidizing agent, e.g., peroxide, is added per volume of sample, and more preferably about 0.5 volumes of oxidizing reagent, e.g., peroxide is added thereto. However, the total dilution of the aliquot sample is less than about 3:1 (v/v) and more preferably less than about 1.8:1 (v/v). In addition, it is preferred that the final concentration of the oxidizing reagent, after addition to the sample, is sufficient to keep the catalyst saturated with oxidzing reagent. This varies depending upon the oxidizing reagent used. For example, the hydrogen peroxide concentration is preferably between 100 and 200 $\mu$mol/L, while the ethyl hydrogen peroxide concentration is preferably between 500 and 2000 $\mu$mol/L. The concentrations of the oxidizing reagent as well as the catalyzing reagent to be added to the sample are determinations within the scope of the skilled artisan without undue experimentation.

The amount of catalyzing reagent that is added to the sample is an amount sufficient to cause the oxidation of up to 50% of the bilirubin present in the sample during the predetermined time for oxidation. The catalyzing reagent utilized is one that has been standardized by techniques known in the art. The preferred concentration of the standardized catalyzing reagent depends upon the type of catalyst used and can be easily determined by the skilled artisan. For type I horseradish peroxidase, the amount used ranges from about 1 $\mu$g/mL to about 50 $\mu$g/mL and more preferably from about 10 $\mu$g/mL to about 30 $\mu$g/mL and most preferably from about 10 $\mu$g/mL to about 25 $\mu$g/mL. The oxidization reaction is then conducted under reaction conditions effective to oxidize a portion (less than about 50%) of the unconjugated bilirubin in said second aliquot for a specified time.

The temperature at which the kinetic portion of the instant method is done is critical because the reaction velocities of the kinetic technique are temperature dependent and because the catalyzing reagent is stable only within certain specified temperature ranges. However, the standardization of the bilirubin catalyzing reagent (e.g., HRP) and the kinetics can be performed at a variety of temperatures as long as the sample analyses are all performed at the same temperature used for standardization. The temperature at which the standardization and the oxidation reaction are conducted range within the temperature range in which the catalyzing reagent is stable. With respect to peroxidase, it is preferred that the temperature of these reaction is conducted at a temperature ranging from about 19° C. to about 40° C. With respect to horseradish peroxidase, a preferable temperature is about 21° C. (at which the $K_p$ is in the range of about eight per minute per $\mu$g/ml HRP). With respect to horseradish peroxide, a more preferable temperature is about 37° C. (at which the $K_p$ is in the range of about 18 per minute per $\mu$g/mL HRP.) In fact, if a peroxidase (e.g., horseradish peroxidase) is the catalyzing reagent, the preferred temperature is about 37° C.

After the oxidation reaction is conducted for a predetermined amount of time, said time being sufficiently short so that the amount of bilirubin oxidized is less than about 50% of the total bilirubin concentration in said second aliquot, the reaction is stopped, by adding for example, a diazo reagent thereto. Utilizing the calorimetric techniques described hereinabove, the amount of unconjugated unoxidized bilirubin remaining after the termination of the catalytic reaction is determined ($B_t$) as described above. In a preferred embodiment, 20 volumes of diazo reagent are added per volume of sample. The diazo reagent initially reacts with the unoxidized conjugated bilirubin for sufficient time to allow reaction of all of the unoxidized conjugated bilirubin and the absorbance thereof read at ~565 nm from which the concentration of the remaining conjugated bilirubin in the sample is calculated by comparing it with a standard curve. Then accelerator is added in sufficient amounts to effect the reaction of the unoxidized unconjugated bilirubin with the diazo reagent, in accordance with the procedure described hereinabove. Preferably, about 20 volumes of accelerator are added per volume of sample. The reaction is allowed to proceed for sufficient time for the remaining unoxidized bilirubin to react with the diazo reagent, as described hereinabove. The absorbance at ~565 nm is read and used to calculate the total bilirubin in the second sample aliquot from a standard curve. Thus, the amount of unoxidized unconjugated bilirubin in the sample ($B_t$) is the difference between the total unoxidized bilirubin in the sample and the unoxidized, conjugated bilirubin of the sample.

MEASUREMENT OF $B_b$

Since a sample may naturally contain other catalysts or other materials that promote oxidation of bilirubin by the added oxidizing reagent, such as peroxide, a control may be utilized to compensate for the amount of bilirubin that undergoes oxidation that is not catalyzed by the added catalyst during the specified reaction time. Thus, a buffer equal in volume to the amount of catalyzing reagent added to the second aliquot is now added to a third aliquot sample containing the same amount of sample and oxidizing reagent, e.g., peroxide, as above in the absence of any catalyzing reagent for the predetermined time specified hereinabove for the second aliquot. Then, the calorimetric reagent, e.g., diazo reagent, is added as before and the amount of unconjugated unoxidized bilirubin ($B_b$) in the sample is determined using the calorimetric techniques as described hereinabove.

A preferred embodiment of the present invention is described hereinbelow. The preferred colorimetric reagents are sulfanilic acid, sodium nitrate and methanol, in the following concentrations:

a. Sulfanilic Acid: 10 g in 15 mL concentrated HCL diluted to 1 L with deionized water.
b. Sodium Nitrite: 0.5 g in 100 mL deionized water
c. 90% absolute methanol/deionized water (v/v)
d. Diazo reagent: 0.05 mL of nitrite per 1.0 mL of sulfanilic acid An exemplary method to measure Bo is described as follow:

1. Diazo reagent is added to sample (20 volumes per volume sample) and the absorbance is read at 565 nm after 1 min. This absorbance is used to calculate direct bilirubin from a standard curve made from known amounts of bilirubin (Sigma Chemical makes an indirect bilirubin standard of about 20 mg/dL). Then 20 volumes of 90% methanol per volume of sample is added and the absorbance is read at 565 nm to determine the total bilirubin.

2. The unconjugated (indirect) bilirubin concentration in the sample is the total bilirubin concentration minus the direct bilirubin concentration.

To determine the steady state unbound unconjugated bilirubin concentration ($b_{ss}$) the following is exemplary of the kinetic/colorimetric method utilized:

1. The indirect bilirubin ($B_o$) of the sample is determined by the diazo method as described above (typically a 25 $\mu$L aliquot of sample).

2. 10 $\mu$L of 67.5 $\mu$g/mL standardized horseradish peroxidase (HRP) and 10 $\mu$L of ethylhydrogen peroxide (final concentration 1.0 mmol/L) is added to a second 25 $\mu$L aliquot of the sample to give a final HRP of 15 $\mu$g/mL.

3. The sample is warmed to 37° C. prior to adding peroxide.

4. After 5 minutes, the diazo reagent is added and the indirect bilirubin ($B_t$) remaining after oxidation is measured, as described above.

5. From these steps, the value of unbound, unconjugated bilirubin in the sample ($b_{ss}$) is calculated from EQ. 1.

An exemplary method to determine $B_b$ (unconjugated bilirubin concentration remaining after any non-peroxidase catalyzed oxidation of bilirubin) is as follows:

6. A third aliquot of sample with 10 μL of Sorensen's buffer instead of HRP is treated as in steps 1–4 above.

7. From steps 1–4 and 6, the value of the unbound, unconjugated bilirubin in the sample ($b_{ss}$) is calculated from EQ. 2.

STANDARDIZATION OF CATALYZING REAGENT

In determining the value of the unconjugated unbound bilirubin in a sample, the catalyzing reagent which is usually peroxidase, e.g., horseradish peroxidase, needs to be standardized. This is done by determining the $K_p$, i.e., the first order rate constant for the oxidation of bilirubin by the oxidizing reagent (usually peroxide) in the presence of the catalyzing reagent. The $K_p$ is determined by standard techniques known in the art, utilizing known concentrations of unbound unconjugated bilirubin. The $K_p$, however, may be determined by measuring the decrease in absorbance of the bilirubin solution over time after the catalytic reagent, e.g., peroxidase, e.g. horseradish peroxidase (HRP), and sufficient oxidizing reagent, e.g. peroxide, to saturate the catalyst, is added to a solution with a known amount of unconjugated bilirubin in the absence of albumin. If B is the unconjugated unoxidized bilirubin concentration at time t, P is the concentration of the catalyzing reagent e.g., peroxidase, $B_o$, and $B_t$ are the initial unconjugated bilirubin concentration and the unconjugated bilirubin concentration at time t, respectively, and the concentration of the oxidizing reagent e.g., peroxide is not rate limiting, then at concentrations of bilirubin that are well below the $K_m$ for peroxidase catalyzed peroxide oxidation of bilirubin, (for HRP, this value is ≅70 uMol at 37° C.), then $$dB/dt = -K_p \cdot P \cdot B \qquad EQ. 3$$

Integrating Equation 3 between the limits t=o and t=t, wherein t is the predetermined time referred to hereinabove provides $$K_p = \frac{\log\left(\frac{B_t}{B_o}\right)}{P \cdot t} \qquad EQ. 4$$

Thus, in accordance with EQ.4, the value of $K_p$ is determined if a known concentration of peroxidase is reacted with an excess amount of peroxide with a known amount of unbound unconjugated bilirubin.

Moreover, it has been determined that when horseradish peroxidase is freeze dried, it is stable for at least 6 months when stored desiccated at −5 to −10° C. Moreover, it has been found that when the freeze dried HRP is reconstituted with water to a concentration of 100 μg/mL, the $K_p$ remains unchanged for up to four weeks.

From the assay, the values of unbound unconjugated bilirubin is calculated from Equations 1 and 2.

The present inventor has found that one of the key advances in the present technology with respect to measuring the oxidation reaction, e.g., the peroxidase method, is the minimal dilution resulting from the addition of the oxidizing reagent and the catalyzing reagent to the aliquot sample. More specifically, the present method does not dilute the sample as much as the prior art. In the prior art method, the sample must be significantly diluted (usually about 1:40). In the present method, the sample is being diluted by addition of the oxidizing reagent and the catalyzing reagent from less than about 3:1 (v/v) and more preferably to a dilution that is less than or equal to about 1.8:1 (v/v).

Dilution has been shown to alter bilirubinalbumin binding by inherently changing the albumin molecule or by diluting out the effects of drugs or endogenous molecules which alter bilirubin-albumin binding.

Another advance in the instant invention is the ability of the present methodology to measure the unbound unconjugated bilirubin fraction. It has been found that HRP can catalyze oxidation of conjugated or direct bilirubin by peroxide in a sample.

If significant amounts of conjugated bilirubin are present in the sample, the concentration of unconjugated unbound bilirubin will be overestimated because the change in bilirubin concentration with time (dB/dt) during oxidation will have significant contributions from both conjugated and unconjugated bilirubin. While the patients with elevated conjugated and unconjugated bilirubin concentrations are still at risk for bilirubin encephalopathy, there is no way of determining what percentage of the change in bilirubin concentration is due to oxidation of neurotoxic unbound unconjugated bilirubin fraction if change in absorption is used to follow the oxidation. Therefore the J & W method alone which uses the change in native bilirubin absorbance to determine unbound bilirubin cannot be used to measure unbound, unconjugated bilirubin concentration in the presence of high concentrations of unconjugated (indirect) bilirubin.

Concentrations of peroxidase recommended in the prior art for bilirubin oxidation yield significantly underestimated unbound bilirubin concentrations because at these peroxidase concentrations, the dissociation of bilirubin from albumin often becomes rate limiting in the reaction. By performing the present assay in accordance herewith, these problems associated with the prior art techniques are overcome.

As a first approximation, for the determination of the unbound unconjugated bilirubin in the sample, $B_b$ need not be measured. Normally, the $B_b$–$B_O$ value is minimal relative to the $B_t$ value; therefore, in order to obtain a first order approximation of the unbound unconjugated bilirubin concentration, the above process is performed without measuring the $B_b$ value. Thus, Equation 1 can be used to solve for $b_{ss}$. To summarize, in this embodiment, only 2 aliquots of sample are required, one to measure $B_o$ and the other the measure $B_t$.

If, in the sample, however, the amount of oxidized bilirubin in the predetermined time (e.g., about 5 minutes or less) is greater than about 50% of the total bilirubin concentration, then $B_b$ ahould be measured.

A fourth aliquot of the sample containing a different (e.g., lower amount) of catalyzing reagent than that used in the third aliquot as shown hereinabove is useful, especially if the rate of dissociation of bilirubin from albumin is rate-limiting (i.e., the rate at which bilirubin dissociates from albumin to replenish the oxidized bilirubin is not substantially faster, e.g. 30 times or more faster than the rate of oxidation of the bilirubin). This can be shown by an equation:

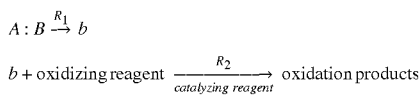

wherein A:B is bilirubin-albumin complex, and is unbound bilirubin. $R_1$ is the rate at which bilirubin is dissociated from albumin and $R_2$ is the rate at which bilirubin is being oxidized. If $R_1$ is not >>$R_2$, then the dissociation of bilirubin from albumin is rate limiting. When $R_1$ is not much greater than $R_2$, the steady state unbound bilirubin from EQ 1 ($b_{ss}$)

will be significantly lower than the true equilibrium unbound bilirubin concentration. Since the rate of bilirubin from albumin is known, one skilled in the art would be able to determine, with out undue experimentation, from the amount of bilirubin oxidized in the predetermined time whether $R_1$ is significantly greater than $R_2$ (See, e.g., Example 4).

When $R_1$ is not much greater than $R_2$, an additional aliquot of sample is required.

On the other hand, if the steady state unbound unconjugated bilirubin concentration measurement at the higher peroxidase concentration is greater than or equal to the steady state unbound unconjugated bilirubin found at the lower peroxidase concentration, then the steady state unbound bilirubin concentration is an accurate estimate of the equilibrium unbound bilirubin concentration, and the two values can simply be averaged, as duplicate samples. If, however, as described above, the steady state unbound bilirubin concentration at the higher peroxidase concentration is lower than that determined at the lower peroxidase concentration, then the rate of dissociation of bilirubin from albumin is rate limiting, and the equilibrium concentration of unbound unconjugated bilirubin $b_{(eq)}$ should be calculated from the steady state unbound bilirubin concentrations as described below. The measurements of the steady state unbound unconjugated bilirubin concentration ($b_{ss}$) at the various peroxidase concentrations are used to calculate the equilibrium unbound unconjugated bilirubin by substitution into the following equation where $k_{-1}$ and $k_1$ are the dissociation and association rate constants for the bilirubin:albumin complex, respectively, and "a" (which remains a constant during the oxidation) is the average concentration of unoccupied bilirubin binding sites:

$$b_{eq} = \frac{k_{-1} \cdot B_o}{k_1 \cdot a} \quad \text{EQ. 6}$$

$$b_{ss} = \frac{k_1 \cdot B_o}{(k_1 \cdot a) + (K_p \cdot P)}$$

where $b_{ss}$ is the steady state unbound unconjugated bilirubin concentration and $k_1$, $B_o$, a, $K_p$ and P are as defined hereinabove.

However, $b_{ss}$ is calculated from EQ 1 or EQ 2 above depending upon whether there is any background oxidation, and a value is determined for each of the different concentrations of the catalyzing reagent tested. These values, $b_{ss1}$ and $b_{ss2}$, which are the steady state concentrations of unconjugated unbound bilirubin, as determined by the use of two different but known standardized peroxidase concentrations, $P_1$ and $P_2$. respectively can be placed into EQ 6 given the following equations $$b_{ss1} = \frac{k_{-1} \cdot B_o}{(k_1 a) + (K_p \cdot P_1)}$$

and $$b_{ss2} = \frac{k_{-1} \cdot B_o}{(k_1 a) + (K_p \cdot P_2)}$$

and $$k_1 a = \frac{(b_{ss1} \cdot K_p \cdot P_1) - (b_{ss2} \times K_p \cdot P_2)}{b_{ss2} - b_{ss1}}$$

$k_1 \cdot a$ can be substituted back into EQ 6 to get $k_{-1}$. The equilibrium concentration of unbound bilirubin is calculated using $k_{-1}$, $k_1 \cdot a$ and $B_o$, $$b_{eq} = (k_{-1} \cdot B_o)/k_1 \cdot a \quad \text{EQ.7}$$

Upon employing more than two catalyzing reagent (e.g., peroxidase) concentrations in the present method, other methods such as linear transformation of equation 6, non-linear regression or median methods nay be used to calculate the equilibrium unbound unconjugated bilirubin concentration when the steady state unbound unconjugated bilirubin concentration decreases with increasing catalyzing reagent concentration.

In another aspect of the present invention, three aliquots of sample are required. In this embodiment, $B_b$ is not measured since the $B_o$–$B_b$ value is minimal relative to $B_t$. However, if in the sample, the dissociation of bilirubin from albumin during the oxidation is rate limiting then it may be necessary to conduct a second oxidation step using a second concentration of the catalyzing reagent as described hereinabove. In this embodiment, one aliquot of a sample is required to measure $B_o$, while the other two samples are used to determine the two $b_{ss}$ values utilizing different concentrations of catalyzing reagent. For each concentration of peroxidase used, $b_{ss}$ is calculated using EX 1.

$$b_{ss} = B_o \cdot \text{Log}\left(\frac{B_t}{B_o}\right) \div (\text{dilution} \cdot K_p \cdot P \cdot t)$$

Thus, if $b_{ss1}$ and $b_{ss2}$ are the steady state concentrations of conjugated non-albumin bound bilirubin, the following equations are applicable:

$$b_{ss1} = (k_{-1} \cdot B_o) \div [(k_1 \cdot a) + (K_p \cdot P_1)]$$

$$b_{ss2} = (k_1 \cdot B_o) \div [(k_1 \cdot a) + (K_p \cdot P_2)]$$

After $b_{ss1}$ and $b_{ss2}$ are determined from the present methodology, and $k_{-1}$ and $k_1 \cdot a$ are determined from solving these two equations, then $b_{eq}$ is determined by Equation 7, in accordance with the present invention.

In another embodiment of the present invention, only 1 aliquot of sample is required. This is applicable when the direct (conjugated) bilirubin concentration in the sample is small and is negligible in comparison relative to the amount of unconjugated bilirubin present in the sample, such as in a newborn, and when the total bilirubin Bo, is known, for example, if it were measured by a previous assay. Under these circumstances, the procedure is as follows:

An aliquot of the sample is mixed with a bilirubin oxidizing reagent and a standardized catalyzing reagent under conditions effective to oxidize the unconjugated bilirubin for a predetermined amount of time sufficiently short so that the amount of bilirubin oxidized is less than about 50% of the total bilirubin concentration, said dilution of said aliquot sample from the addition of said oxidizing and catalyzing reagent being less than about 3:1 by volume. The oxidation reaction is stopped at the predetermined amount of time and the concentration of unconjugated bilirubin is determined. In a preferred embodiment the diazo reagent and acid and accelerator are added. It is to be noted that since in this embodiment it is assumed that the concentration of conjugated bilirubin is small, there is no need to add the diazo reagent and acceleration in two steps. In this embodiment, they can be added almost simultaneously. The absorbance is read at ~565 nm and is used to calculate the amount of bilirubin present in the sample. Since the sample contains little conjugated bilirubin, the value obtained from the standard curve is the unconjugated unoxidized bilirubin in the sample ($B_t$).

Therefore, in this embodiment $$b_{ss} = -B_o \cdot \text{Log}\left(\frac{B_t}{B_o}\right) \div (\text{dilution} \cdot K_p \cdot P \cdot t)$$

The terms "UUBC" and "Bu" are synomous and are used interchangeably.

The following non-limiting examples further illustrate the present invention.

EXAMPLE 1

Procedure for Measuring Unbound Unconjuaated Bilirubin by Combining the Peroxidase and Diazo Tests (deroxidase-diazo test):

Samples to be analyzed were divided into at least two aliquots of as little as 10 μL each, depending on available sample volume. The first aliquot was used to measure the initial unconjugated bilirubin concentration ($B_o$) by the diazo method. The second aliquot was used to measure the indirect bilirubin concentration remaining ($B_t$) after t minutes of ethyl hydrogen peroxide oxidation catalyzed by horseradish peroxidase (HRP). A third aliquot was used to measure the unconjugated bilirubin remaining ($B_{t_b}$) after t minutes of oxidation of bilirubin by peroxide in the absence of peroxidase to control for any non-HRP catalyzed oxidation. This is minimal in most samples. $B_t$ can be measured in additional aliquots at one or more additional HRP concentrations when necessary to correct for rate limiting dissociation of the bilirubin-albumin complex.

HRP (or buffer in controls without the catalyst) was added to give a final concentration typically between 1 and 150 μg/ml.

The aliquots were warmed to 37° C. in a water bath and peroxide added to a final concentration of 200 μmol/L for hydrogen peroxide or 600–1000 μmol/L for ethyl hydrogen peroxide to start the reaction. The volumes of peroxide and HRP selected along with the sample volume determine the dilution at which the unconjugated unbound bilirubin concentration is measured. Sample dilutions <1:3 (sample volume:reaction volume) were used.

After t minutes of oxidation (0 min for aliquot 1 and 1 to 5 min for the other aliquots, the reaction was stopped by adding sulfanilic acid, which denatures the HRP and is also the initial reagent for the diazo test. The remaining indirect bilirubin concentration ($B_{t_b}$) or ($B_t$) is measured by the diazo test. Since the diazo test measures both the total bilirubin concentration TBC and the unconjugated bilirubin concentration, the results can be used to calculate both the unconjugated unbound bilirubin and total unbound bilirubin as outlined above by using either the unconjugated bilirubin concentrations or the total bilirubin concentration, respectively.

EXAMPLE 2

Effect of Conjugated Bilirubin on UUBC:

The effect of conjugated (direct) bilirubin on UUBC determination was investigated in plasma from two newborns and two adults having hyperbilirubinemia.

Total unbound bilirubin (TUBC) and unbound unconjugated unbound (UUBC) determination were analyzed using the present methods in two newborns sera, one with (Sample A) and one without (Sample B) high conjugated bilirubin concentrations. Sample A is from a baby weighing 750 g who at 1 month of age was afflicted with cholestasis. Albumin concentration was 2.4 g/dL. The oxidation was carried out for 1 min with $K_p$ of the horseradish peroxidase being 17.6 mL·min$^{-1}$μg$^-$. Sample B is from a one month old premature weighing 1640 g who developed unconjugated hyperbilirubinemia following a blood transfusion. Albumin is 3.0 g/dL, $K_p$ =17.7 mL/min·μg, and dilution 1:2.2.

The TUBC and UUBC were determined in accordance with the present invention. The results are tabulated in Table 1 for Sample A. The factor 0.0585 in the denominator is used to convert the units of bilirubin concentration from mg/dL to u molar/L.

TABLE 1

| Sample | time (min.) | HRP (μg/mL) | total bilirubin (mg/dL) | conjugated (mg/mL) | unconjugated (mg/dL) | TUBC | UUBC |
|---|---|---|---|---|---|---|---|
| A | 0 | 10.0 | 12.4 | 7.1 | 5.3 | 0.015 | 0.006 |
|   | 1 | 0.0 | 9.7 | 5.5 | 4.2 |   |   |
|   | 1 | 10.0 | 4.4 | 2.4 | 2.0 |   |   |
| CALCULATIONS OF SAMPLE A: ||||||||
| $$\text{UUBC} = \frac{5.3 \cdot \log\frac{(5.3 + 2.0 - 4.2)}{5.3}}{0.0585 \cdot 10 \cdot 17.6 - 43.7 \cdot 1} = 0.006 \ \mu\text{mol/L}$$ ||||||||
| $$\text{TUBC} = \frac{12.4 \cdot \log\frac{(12.4 + 4.4 - 9.7)}{(7.1 + 5.3)}}{0.0585 \cdot 10 \cdot 17.6 - 43.7 \cdot 1} = 0.015 \ \mu\text{mol/L}$$ ||||||||
| B | 0 | 15.4 | 15.2 | 1.3 | 13.9 | 0.113 | 0.104 |
|   | 1 | 0.0 | 15.2 | 1.2 | 14.0 |   |   |
|   | 1 | 15.4 | 11.7 | 0.5 | 11.2 |   |   |

The UUBC by calculated was 0.006 μmol/L, while the TUBC calculated was 250% higher at 0.015 μmol/L.

The UUBC from a newborn without much direct bilirubin present is also shown in Table 1 (Sample B) for comparison. In this newborn, the TUBC is only about 8% higher than the UUBC.

Similar studies were done using adult sera with elevated direct reacting bilirubin, as follows:

UUBC and TUBC in two adult sera with high direct bilirubin concentrations were measured in accordance with the methodology of the present invention. Albumin concentrations were 3.0 g/dL in sample A and 2.2 g/dL in sample B. The peroxidase concentration was 1.85 μg/mL, the $K_p$ 18.5 mL/min per μg peroxidase, the dilution 1:2.4, and the reaction time 5 min. The TUBC was calculated using the total bilirubin concentration (unconjugated +conjugated bilirubin concentrations) and the UUBC was calculated using only the toxic unconjugated bilirubin concentrations.

The results are provided in Table 2.

TABLE 2

| Sample | time (min) | HRP (μg/dL) | Bilirubin | | | | |
|---|---|---|---|---|---|---|---|
| | | | total bilirubin (mg/dL) | direct (mg/dL) | Indirect (mg/dL) | TUBC (μmol/L) | UUBC (μmol/L) |
| A | 0 | 1.85 | 13.9 | 8.7 | 5.2 | 0.208 | 0.026 |
| | 5 | 1.85 | 9.3 | 4.7 | 4.6 | | |
| | 5 | 00.0 | 13.5 | 7.5 | 6.0 | | |
| B | 0 | 1.85 | 11.9 | 4.7 | 7.2 | 0.285 | 0.192 |
| | 5 | 1.85 | 5.2 | 2.0 | 3.2 | | |
| | 5 | 0.00 | 10.4 | 3.8 | 6.6 | | |

The TUBC which includes both the unbound conjugated and unbound unconjugated bilirubin concentrations, were 0.208 μmol/L for A and 0.285 μmol/L for B, respectively and would suggest that the patients would be at equal risk for bilirubin toxicity. However, the UUBCs between the two samples are substantially different (0.024 μmol/L for A and 0.192 μmol/L for B). The UUBCs indicate that patient B is at significantly higher risk for bilirubin toxicity.

EXAMPLE 3
Levels of Unbound Bilirubin which are Toxic

Using the methodology of the present invention, 9 unbound bilirubin measurements in newborns were made. The TOTAL bilirubin levels were similar in all of them. One of them was sick with bilirubin encephalopathy documented by an abnormal hearing screen. All the rest were well. The unbound bilirubin was substantially higher in the sick newborn.

| Total bilirubin (mg/dL) | Unbound bilirubin (μmol/L) | Comments |
|---|---|---|
| 23.0 | 0.250 | Bilirubin encephalopathy |
| 21.6 | 0.060 | Well |
| 21.7 | 0.100 | Well |
| 20.3 | 0.070 | Well |
| 31.3 | 0.091 | Well |
| 19.9 | 0.020 | Well |
| 20.1 | 0.009 | Well |
| 26.4 | 0.042 | Well |
| 22.5 | 0.110 | Well |

As can be seen, the mean unbound of the well babies is 0.063 μmol/L ±0.037 while that of the sick baby is 4 times higher.

This experiment shows that high values of unbound unconjugated bilirubin concentration in the sample correlate well with bilirubin toxicity and low values correlate well with no evidence of bilirubin toxicity. When performing tests on test samples, it is preferable that the results be compared with values of the test from patients with similar total bilirubin concentrations who do not have evidence of bilirubin toxicity. If the value from test sample is significantly greater, e.g., about two-fold or about two standard deviations above the normal values, then it is concluded that the patient from whom the sample was obtained is of significant risk for developing bilirubin toxicity.

EXAMPLE 4
Conditions for Determining When Controls are Needed for Peroxidase-Diazo Test The accuracy of the peroxidase scheme for measuring unbound bilirubin relies on minimal perturbation of the underlying dynamic equilibrium of bilirubin and albumin (it is assumed that all the bilirubin is unconjugated) where A:B is the concentration of the bilirubin-albumin complex, $b_{eq}$ is the equilibrium unbound bilirubin concentration, and a is the equilibrium unbound albumin concentration:

$$A:B \rightarrow a + b_{eq}$$

When HRP and peroxide are added to the system, the unbound bilirubin is oxidized and the system shifts from an equilibrium to a steady state according to the following scheme:

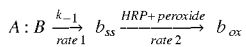

where $b_{ss}$ is now the steady state of unbound bilirubin and box represents the oxidation products of the reaction. It is preferred that rate 1 is very fast compared to rate 2. If the dissociation of the A:B complex, governed by the first order dissociation rate constant $k_{-1}$ (the rate of the dissociation of the complex is $k_{-1} \cdot A:B$), is very fast compared with the rate of oxidation which is $K_p \cdot HRP \cdot b_{ss}$ (e.g. the complex dissociates about 20 times faster than the oxidation rate), then the $b_{ss}$ will be very nearly equal to the $b_{eq}$ (e.g. about 95% of $b_{eq}$ if the A:B dissociation is 95% faster than the rate of oxidation).

It has been established that the lowest value for $k_{-1}$ is about 0.4/min. Therefore, the relationship between the amount of bilirubin oxidized over a period of time and the necessity of needing to do the controls can be established. This is done using the general equation:

$$\log\left(\frac{B_t}{B_o}\right) = -k_{-1} \cdot \text{time}$$

A table for the longest time that it would take the complex to dissociate assuming 0.4/min for $k_{-1}$ can be constructed as follows:

| $B_t/B_o$ | % Dissociated | Time required(s) |
|---|---|---|
| 0.95 | 5% | 7.7 |
| 0.90 | 10% | 26.3 |
| 0.80 | 20% | 33.5 |
| 0.70 | 30% | 53.5 |

Using the above data and establishing that the oxidation rate is no more than 5% of the dissociation rate, it can be determined how much the actual bilirubin concentration can decrease over a given period of time before determining whether controls are necessary.

For example, if more than 20% of the bilirubin is oxidized before 670 s (11.2 min) has elapsed, then it is likely that the rate of oxidation is not 20 times slower than the rate of dissociation. As another example, if more than 5% of the bilirubin is oxidized in 154 s (2.6 min) then again it is likely that the dissociation of bilirubin from albumin is significantly rate limiting, reducing beq to steady state values, bss, that may be significantly below the true (equilibrium) unbound bilirubin concentration in the sample. Considering the error of the method, it would be greater than 95% of the equilibrium unbound bilirubin. This can be determined by noting the amount of bilirubin oxidized during the time interval selected for the reaction. If the amount oxidized exceeds that allotted (see Table above), controls (i.e. determination of unbound bilirubin at additional peroxidase concentrations and determination of whether non-peroxidase catalyzed oxidation of bilirubin is taking place) are necessary.

EXAMPLE 5

Effect of Rate Limiting Dissociation of Bilirubin from its Albumin Complex on UUBC:

The HRP concentration was varied between about 1 and 125 $\mu$g/ml in plasma samples from 20 jaundiced newborns. The ratio of the steady state UUBC to equilibrium UUBC is plotted as a function of HRP concentration in FIG. 1. The ratio decreases significantly with increasing HRP concentration indicating increasing underestimation of the UUBC as HRP concentration increases. Even at very low HRP concentrations, there was still significant underestimation of UUBC in some samples, indicating that at least two HRP concentrations may need to be used when analyzing samples. Furthermore, HRP concentrations below about 5 $\mu$g/ml were not practical because the non-HRP catalyzed oxidation background often becomes a significant portion of the overall rate of oxidation reducing the precision of the assay. Thus, from the change in unconjugated bilirubin concentration over the time of oxidation, one can determine whether a measurement of unbound bilirubin concentration at additional horseradish peroxidase concentrations are required.

EXAMPLE 6

MEASUREMENT OF UNBOUND UNCONJUGATED BILIRUBIN IN A SAMPLE WITH HIGH LEVELS OF CONJUGATED BILIRUBIN

The instant invention has the advantage of detecting and correcting for high levels of conjugated bilirubin in a sample in contrast to methods which only measure total unbound bilirubin. The confounding effects of the oxidation of conjugated bilirubin can lead to overestimation of the toxic unbound bilirubin fraction. The instant methodology also corrects for any rate limiting dissociation of bilirubin from albumin which can lead to an underestimation of the toxic unbound bilirubin fraction. These features are illustrated in the following example demonstrating errors resulting from failing to differentiate conjugated and unconjugated unbound bilirubin in a sample. In this example, the value of dissociation of bilirubin from albumin is rate limiting, and measurements were made at two different peroxidase concentrations.

Solutions:
Buffer: 0.055M Sorensen's phosphate buffer, pH 7.4.
Standard: 1. Sigma Chemical bilirubin control (unconjugated bilirubin only): total bilirubin 19.9 mg/dL, conjugated bilirubin 0 mg/dL.
Sample: 2. ChemTrak 3 control serum with total bilirubin about 15 mg/dL and conjugated bilirubin about 4 mg/dL.
Peroxidase: 3. Standardized horseradish peroxidase (HRP): 80 $\mu$g/ml and 160 $\mu$g/ml in 0.055M Sorensen's phosphate buffer, pH 7.4. $K_p$=20.9 per min per $\mu$g/ml at 37° C.
4. Ethyl hydrogen peroxide (EtOOH), 10 mM in 0.055M Sorensen's phosphate buffer.
Diazo: 5. Sulfanilic Acid 10 g/L in 1 liter of water containing 15 ml of concentrated HCL.
6. Sodium nitrite 0.5 g in 100 ml water
7. Methanol/water 90% v/v.
Kinetic Reaction:
1. Sample 0.05 ml
2. Buffer or HRP 0.05 ml (final HRP=36.4 and 72.8 $\mu$g/ml for the 80 and 160 $\mu$g/ml stocks, respectively).
3. Buffer or EtOOH 0.01 ml HRP was added to the sample in the reaction vessel and warmed to 37° C. EtOOH was added and the reaction stopped after 1 min by adding 1.0 ml of sulfanilic acid. The sample solution was transferred to a cuvette and the cuvette is blanked at 566 nm in an HP 8452 spectrophotometer. Nitrite (0.050 ml) was added and the absorbance measured (566 nm) after 1 min. This absorbance value was used to calculate the concentration of conjugated bilirubin in the sample. Methanol (1.0 ml) was subsequently added and after mixing, the absorbance was again determined (566 nm) after 2 min. This second absorbance value was used to determine the concentration of total bilirubin in the sample. The concentration of unconjugated bilirubin in the sample was determined by subtracting the value for the concentration of total bilirubin from the value for the concentration of conjugated bilirubin.

The Sigma standard was used to determine the extinction coefficient for diazo derivatives at 566 nm (reaction vessel 1). It was processed similarly to the reactions, but no bilirubin oxidizing reagent or bilirubin oxidation catalyzing reagent (e.g., EtOOH or HRP) was added. The concentrations for the total, conjugated, and unconjugated bilirubin in the ChemTrak sample was measured before and after oxidation. There was no oxidation of bilirubin by peroxide in this sample in the absence of peroxidase. The preoxidation bilirubin concentration was determined in the same manner as the Sigma standard (reaction tube 2). The oxidation was allowed to proceed at the two different HRP concentrations in tubes 3 and 4 for 1 minute.

| | | REACTIONS | | | |
|---|---|---|---|---|---|
| VES- | | HRP ml | | BUFFER | EtOOH |
| SEL | SAMPLE ml | 80 $\mu$g/ml | 160 $\mu$g/ml | ml | ml |
| 1 | Sigma 0.05 | — | — | 0.06 | — |
| 2 | ChemTrak 0.05 | — | — | 0.06 | — |
| 3 | ChemTrak 0.05 | 0.05 | — | — | 0.01 |
| 4 | ChemTrak 0.05 | — | 0.05 | — | 0.01 | after 1:00 minute (vessels'3 and 4) 0.1 mg of sulfanilic acid +0.05 ml of nitrite followed by +1.0 ml of methanol were then added as described above.

| | RESULTS | | |
|---|---|---|---|
| | | BILIRUBIN mg/dL | |
| TUBE | TOTAL | CONJUGATED | UNCONJUGATED |
| 1 | 19.9 | 0 | 19.9 (standard) |

-continued

RESULTS

| TUBE | TOTAL | BILIRUBIN mg/dL CONJUGATED | UNCONJUGATED |
|---|---|---|---|
| 2 | 15.1 | 4.2 | 10.9 |
| 3 | 12.7 | 2.0 | 10.7 |
| 4 | 11.6 | 1.1 | 10.5 |

Calculation of unbound bilirubin considering only total bilirubin concentration per (Jacobsen and Wennberg; 1974):

For HRP=36.4 $\mu$g/ml; Initial total bilirubin ($B_o$)=15.1 mg/dL. (MW for bilirubin=585 grams/Mole) and to convert bilirubin to a $\mu$mole/L, the mg/dL concentration is divided by 0.0585.

Net change in total bilirubin ($B_t$)=12.7 mg/dL (total in tube 3) steady state unbound bilirubin (bss) formula:

$$b_{ss} = -\frac{Bo \cdot \log\left(\frac{B_t}{B_o}\right)}{K_p \cdot HRP \cdot t \cdot \text{dilution} \times 0.0585}$$

teady state total unbound (conjugated+unconjugated) bilirubin=0.027 $\mu$M which is about 0.01% of the total ilirubin concentration of 15.1 mg/dL (258 $\mu$M).

For HRP=72.8, the steady state unbound bilirubin was calculated as outlined above wherein:

$B_o$ is 15.1 mg/dL and $B_t$ is 11.6 mg/dL, given a steady state unbound bilirubin is 0.020 $\mu$M.

Since the steady state unbound at the higher HRP is less than that at the lower HRP, the dissociation of bilirubin from albumin must be rate limiting during the oxidation.

Solving the equation as described above gives an equilibrium unbound bilirubin of 0.042 $\mu$mol/L. Thus, without correcting for the rate limiting discussion of bilirubin from albumin, the unbound bilirubin is underestimated by approximately 36%. The necessity of correcting for this problem would only become apparent when performing the test at two or more HRP concentrations. Using this as an example, an additional potential error occurs because no correction is made for the oxidation of conjugated as well as unconjugated bilirubin. If the conjugated bilirubin is subtracted from each total bilirubin to get the unconjugated (toxic form) of bilirubin (last column in the results table), then the unconjugated unbound bilirubin is calculated as outlined above using the unconjugated bilirubin values:

For HRP=36.4 $\mu$g/ml, $B_o$ is 10.9 mg/dL (total unconjugated bilirubin) and $B_t$ is 10.7 mg/dL, given a steady state unbound, unconjugated bilirubin is 0.002 $\mu$M.

For HRP=72.7 $\mu$g/ml, $B_o$ is 10.9 mg/dL (total unconjugated bilirubin) and $B_t$ is 10.5 mg/dL, given a steady state unbound, unconjugated bilirubin is 0.002 $\mu$M.

Note that since the unbound, unconjugated bilirubin is the same at each HRP the dissociation of unconjugated bilirubin from albumin is not rate limiting in this reaction. Note further, that without taking into account the interference of the conjugated bilirubin, the toxic bilirubin fraction would be mistakenly identified at a value approximately 40 times greater than its actual value. There is no indication of rate limiting dissociation of bilirubin from albumin after correcting for the interference from conjugated bilirubin. The dilution used for the determination of unconjugated unbound bilirubin in this example is 1:2.2. The advantages of the instant technology for measuring unconjugated unbound bilirubin as compared with methods that cannot differentiate conjugated and unconjugated unbound bilirubin is clear. Additionally, if only one bilirubin oxidizing catalyst concentration (e.g., only one HRP concentration) is used in this instance, the concentrations of unbound bilirubin in a sample can be seriously underestimated.

EXAMPLE 7

Measurement of Unbound Unconjugated Bilirubin Brainstem Auditory Evoked Potential in Gunn Rat Pups.

Bilirubin toxicity produces, inter alia, deafness. It has been shown that bilirubin induces specific changes in the brainstem auditory evoked potential (BAEP), a test used to assess hearing in the newborns. The BAEP has been proposed as a method for assessing when a newborn is a risk for bilirubin toxicity.

Recently it has been shown that changes in BAEP correlate better with measures of unbound bilirubin concentration (measured by W & J test), than with the total bilirubin concentration in human neonates.

The unconjugated unbound concentration and BAEPs were measured by the present method in homozygous (jj) Gunn rat pups. (an animal with congenital unconjugated hyperbilirubinemia which serves as a model for neonatal jaundice). While the W & J method has been used to measure bilirubin-albumin binding in this animal, serum turbidity, need for sample dilution, and variable absorbance characteristics limit the accuracy of the test. The results from the method of the present invention were compared with the BAEPS measurements.

Brainstem Auditory Evoked Potentials (a sensitive indicator of bilirubin toxicity) were measured on Gunn rat pups who weighed 26.8 g (SD 2.0) at 16.0 days of age (SD 0.5). BAEPs were measured under ketamine and acepromazine anesthesia. Seventy-five dBHL monaural clicks were administered to the right and left ears and the I-II interwave interval (BAEP wave II latency—BAEP wave I latency) from the right and left ears was averaged. This interval is a sensitive indicator of bilirubin toxicity.

Following measurement of the I-II interwave interval, blood was obtained by cardiac puncture for analysis of bilirubin-albumin binding.

Serum was separated and frozen at −70° C. until analysis.

The albumin was measured by BCP method using rat albumin (Sigma Chemical Company) as standard. At 10 $\mu$L aliquot was combined with 2 ml of BCP. The absorbance of rat albumin and BCP at 604 nm is about 50% of that for human albumin.

The total bilirubin concentration (these animals make no conjugated bilirubin) was measured by the diazo method using 25 $\mu$L of Serum. A Sigma unconjugated bilirubin control was used for a standard. This method corrects for turbidity as the cuvette is zeroed after adding the sample but before adding the nitrite and methanol.

Twenty-five $\mu$L of rat serum was then mixed with 25 $\mu$L of HRP and 10 $\mu$L of a 1:160 dilution of 10–12% ethyl hydrogen peroxide and the oxidation allowed to proceed for 1 to 3 minutes. The reaction was stopped with the diazo sulfanilic acid reagent which denatures the HRP. The sample was placed in the spectrophotometer which was zeroed, and nitrite and methanol added. $B_t$ was calculated from the absorbance of the diazotized sample after 2 min. The $b_{ss}$ was calculated by equation 1.

The $b_{ss}$ was determined from measurements at 3 to 4 different HRP concentrations between 0.3 and 67 $\mu$g/ml to correct for rate limiting dissociation of bilirubin from albumin and the $b_{ss}$ values were used to calculate the equilibrium unbound bilirubin ($b_{eq}$) hereinabove.

Figure 4:
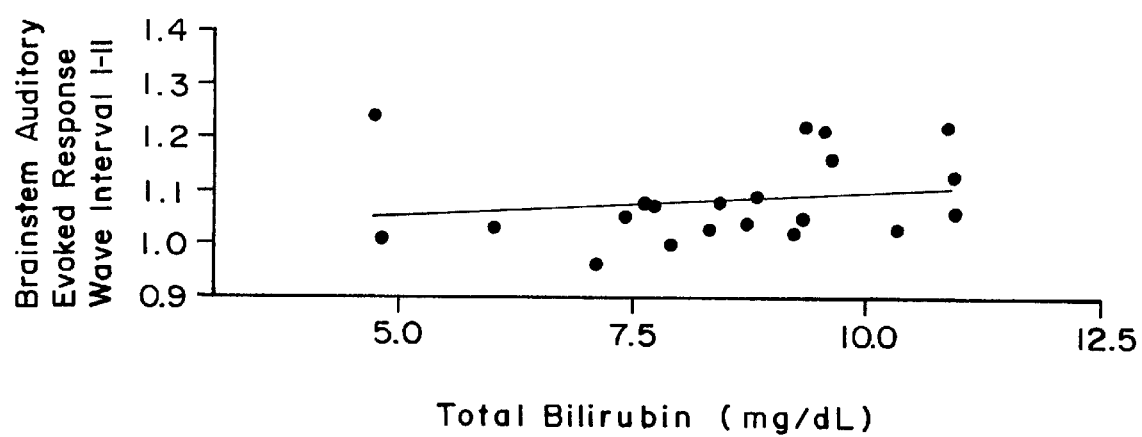
FIG. 4 shows graphically that there is no significant correlation between the total Bilirubin concentration and the changes in brainstem auditory evoked potential wave I-II interval in homozygous Gunn rat pups. ($r^2=0.045$).
Figure 5:
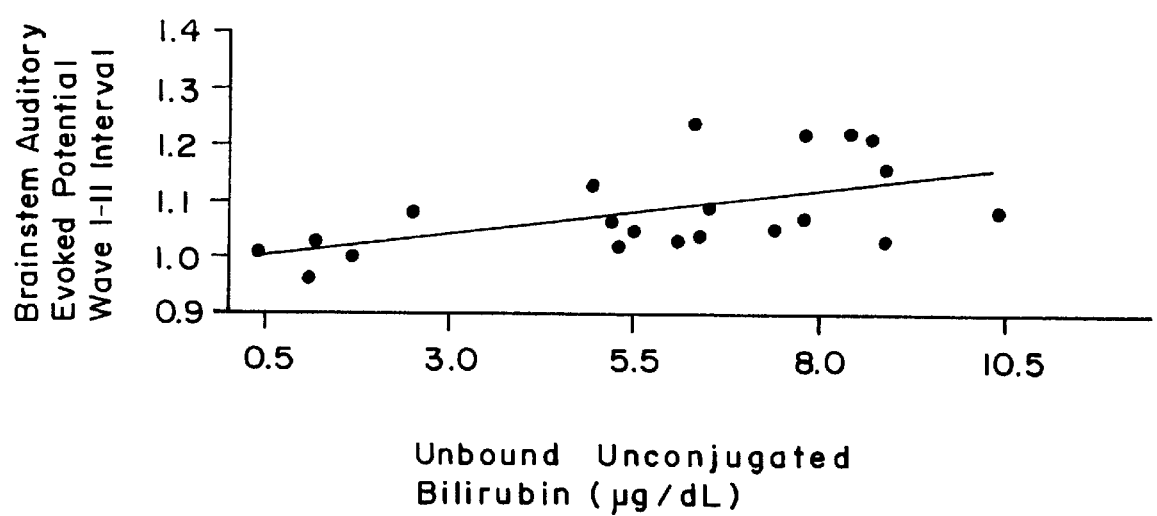
FIG. 5 depicts graphically the positive correlation between the unconjugated unbound bilirubin concentration and the changes in brainstem auditory evoked potential wave I-II interval in homozygous Gunn rat pups. ($r^2$=0.31).

The results from the two methods are shown in FIGS. 4–5, which compare BAEP changes and function of the total bilirubin concentrations and UUBC.

FIG. 4 shows no significant correlation with Total Bilirubin ($r^2=0.045$).

FIG. 5 shows significant correlation of with unbound unconjugated bilirubin ($r^2=0.31$).

EXAMPLE 8

THE EFFECT OF SAMPLE DILUTION ON MEASUREMENTS OF THE CONCENTRATION OF UNBOUND BILIRUBIN

As previously described, direct testing of bilirubin is preferred to indirect testing. However, direct testing for the concentration of unbound, unconjugated bilirubin in a sample is sensitive to the sample dilution used. The following example illustrates how large dilutions of a sample (i.e., in the range of about 1:40) in a direct test for the concentration of unbound, unconjugated bilirubin in a sample can lead to an underestimation of the true value of unbound, unconjugated bilirubin in the sample. The drug sulfisoxazole, which displaces bilirubin from albumin, has been reported to result in the development of bilirubin toxicity when given to newborns, presumably as a consequence of increasing the concentration of unbound, unconjugated bilirubin in the blood and tissues of the neonate (Silverman W A et al, *Pediatrics* 18:614, 1956). Using this fact, Applicant attempted to determine if altering the sample dilution in an in vitro, direct test would influence the determination of the concentration of unbound, unconjugated bilirubin. The in vitro test was employed since known concentrations of reagents could be used and the amount of unbound bilirubin in the test manipulated. Sulfisoxazole was employed, as reported by Silverman, as a means of removing bilirubin that was bound to albumin, thus increasing the level of unbound, unconjugated bilirubin in the sample. It was hypothesized that these increases in the concentration of unbound, unconjugated bilirubin would be more accurately measured using the instant methods which use small sample dilutions (i.e., a dilution in the range of about 1:2) than using a direct method which required a large sample dilution (i.e., a dilution in the range of about 1:40).

Two sample dilution concentrations were used (1:1.8 and 1:41.8). The higher sample dilution (1:41.8) was chosen because it is in the range of the reported dilution required in the unbound bilirubin assay method of Jacobsen and Wennberg (*Clin. Chem.* 20:783, 1974). The lower sample dilution represents the direct assay method employed in the instant invention.

Solutions of unconjugated bilirubin in defatted albumin (total bilirubin 20 mg/dL, total albumin 3.0 g/dL) were analyzed with and without the presence of 15 mg/dL sulfisoxazole. This concentration of sulfisoxazole was employed since it mimicked the blood levels of sulfisoxazole reported by Silverman (i.e., 15 mg/dL).

Sulfisoxazole (0.025 ml of 6 mg/dL) or buffer (0.025 ml) was added to 0.975 ml of a 3.0 g/dL defatted albumin solution containing approximately 20 mg/dL bilirubin in 0.055M Sorrensen's buffer @ pH 7.4. Final sulfisoxazole concentration was 15 mg/dL. The peroxidase technique as described hereinabove was used to measure the unbound bilirubin concentrations at 1:1.8 and 1:41.8 dilutions using the instant method compared with the method of Jacobsen and Wennberg. A 0.1 cm path cuvette was employed to allow direct spectral analysis of the unbound bilirubin at the 1:1.8 dilution.

Methods: The 1:1.8 dilution readings were made as follows:

100 $\mu$l of bilirubin-defatted albumin sample was added to a 0.1 cm path cuvette containing 40 $\mu$l of 16 $\mu$g/ml standardized HRP ($K_p=19.6$ ml/min $\mu$g). The HRP and EtOOH were contained in 0.055M Sorensen's buffer, pH 7.4. The final HRP concentration was 3.56 $\mu$g/ml. The fall in absorbance measured at 460 nm was monitored for more than five minutes. The concentration of unbound bilirubin was calculated from the first order change in the total bilirubin concentration after the time period using EQ.1.

No interference from rate limiting dissociation of bilirubin from albumin was discovered when HRP concentration was approximately doubled.

Colorimetric method: 10 $\mu$l each of HRP and EtOOH (in a concentration and molarity as described above) was added to 25 $\mu$l samples of bilirubin-defatted albumin solutions with and without added sulfisoxazole. After five minutes, 0.5 ml of a diazo reagent (sulfanilic acid+nitrite) was added to stop the reaction (the conjugated bilirubin concentration was not measured as none is present in this artificial system). Subsequently, 0.5 ml of 90% methanol was added to accelerate color formation. A similar sample containing 10 $\mu$l of buffer instead of HRP was used to determine the total bilirubin concentration at time zero (t=0). The unbound bilirubin concentration was calculated using the equation (1).

The 1:41.8 dilutions were made by adding 0.025 ml of sample to 1.0 ml of buffer and starting the reaction with 10 $\mu$l each of EtOOH and HRP as above. The Jacobsen and Wennberg method was performed as above using a 1 cm path cuvette. The calorimetric technique was performed by stopping the reaction after five minutes with 1.0 ml of diazo-A and then adding 1.0 ml of 90% methanol. The results are presented in Table 3.

TABLE 3

| CONCENTRATION OF UNBOUND BILIRUBIN ($\mu$m) | | | |
|---|---|---|---|
| Dilution | Method | + Sulfa | − Sulfa |
| 1:1.8 | Instant Invention | 0.285 ± 0.03 | 0.135 ± .005 |
| 1:41.8 | W & J method | 0.092 ± .003 | 0.098 ± .027 |

Values are given as the mean and standard deviation of 3 replicates.

As demonstrated in Table 3, assays employing minimal dilutions (i.e., 1:1.8) more accurately reflect the concentration of unbound, unconjugated bilirubin released by sulfisoxazole. Assays that employ higher sample dilutions (i.e., 1:40) did not detect the effect of sulfisoxazole on unbound bilirubin. Increases in the amount of unbound, unconjugated bilirubin released after applications of sulfisoxazole were approximately twofold. Such a finding is extremely significant since the toxic fraction of total bilirubin is represented within the portion that is made up of the unbound, unconjugated bilirubin species. Therefore, a method with increased sensitivity for detecting an increase in the concentration of unbound, unconjugated bilirubin will be extremely useful and advantageous. Increased sensitivity to the smallest change in the concentration of unbound, unconjugated bilirubin is beneficial since, as the binding sites of albumin for bilirubin become saturated, further small increases in total bilirubin concentration may be accompanied by disproportionately large changes in the concentration of unbound, unconjugated bilirubin which is neurotoxic. Therefore, even small increases in the concentration of total bilirubin can place a newborn infant at a substantial risk for developing bilirubin encephalopathy. Accordingly, an assay which is sensitive to even small increases in the amount of unbound, unconjugated bilirubin is preferred to an assay which is unable to detect elevated levels of unbound bilirubin produced by small changes in total bilirubin or by molecules capable of interfering with bilirubin-albumin binding.

EXAMPLE 9

Figure 3:
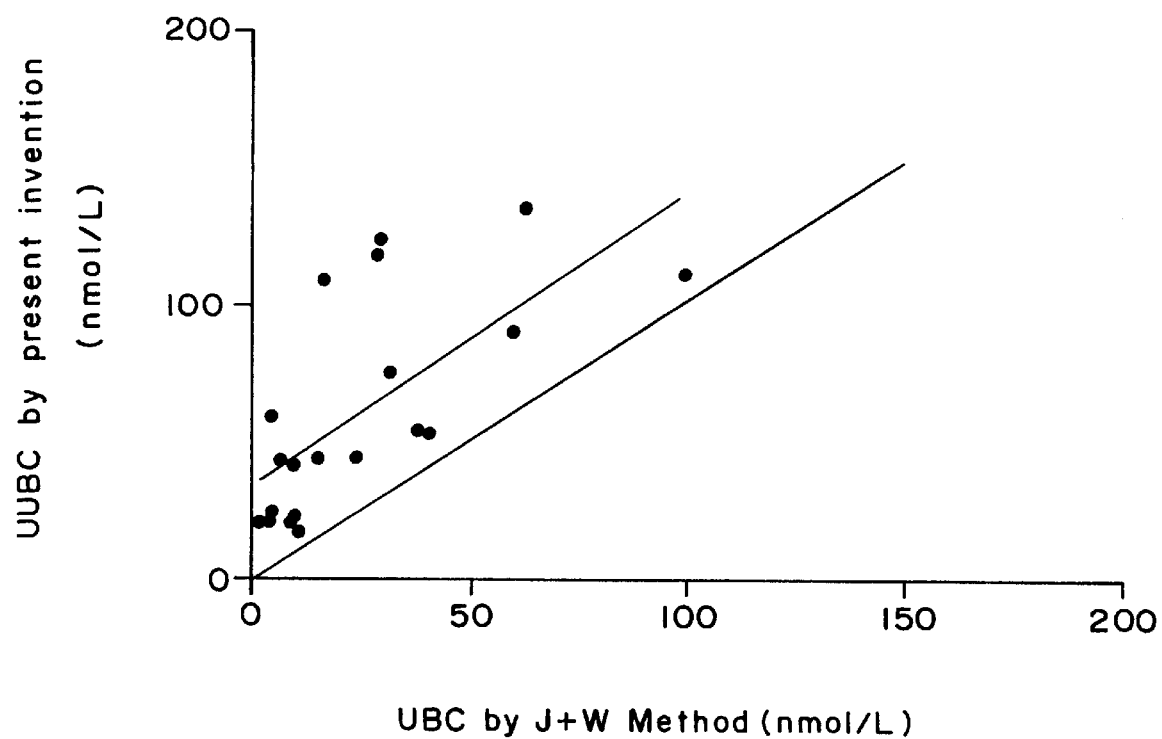
FIG. 3 depicts graphically the correlation of the value obtained by the W & J method for unbound bilirubin concentration (UBC) at a 1:40 sample dilution with that value (UUBC) determined by the present invention at a 1:1 sample dilution. The UBC determined by the J & W method contains both conjugated and unconjugated unbound bilirubin fractions, while the present method measures only the unbound unconjugated bilirubin fraction. The lower line is unity. The upper line is the regression curve.

Comparison of the Present Method For Measuring UUBC With The Method of Jacobsen & Wennbera Plasma UUBC was measured in 20 newborns by the present invention and the value obtained was compared when the W & J method was used to measure the UBC values. For the W & J method, 4 HRP concentrations were used with a sample dilution of 1:43.7, and for the present invention a 1:1.8 sample dilution and 2 to 4 peroxidase concentrations were used. The results are shown in FIG. 3. The values obtained from the present invention more accurately measured the UUBC.

EXAMPLE 10

UUBC in Plasma of a Newborn Determined by the Instant Invention.

Figure 2:
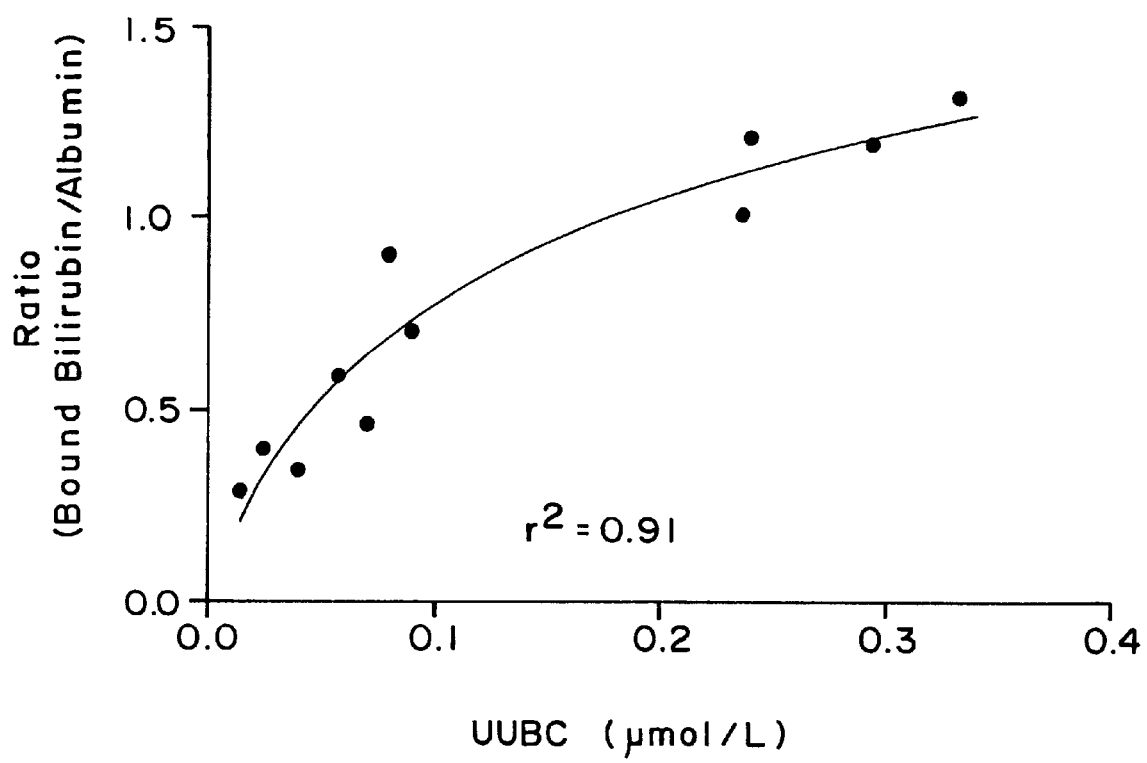
FIG. 2 is a binding isotherm plotting the ratio of bound bilirubin to albumin in a newborn as a function of unconjugated unbound bilirubin concentration (UUBC) measured in accordance with the methodology of the present invention and a sample dilution of 1:1.8. The curve was fited to a two-site equilibrium binding model using non-linear regression.

Plasma from a partial exchange transfusion performed in a term newborn with polycythemia was titrated with bilirubin and the unconjugated unbound bilirubin determined by the present method to assess the bilirubin-albumin binding isotherm in minimally diluted plasma. The results are shown in FIG. 2. Non-linear regression used to determine the equilibrium binding constants, and a two-site model with interaction between sites best fit the binding isotherm. The equilibrium dissociation constant for the 1:1 bilirubin/albumin species was 0.059 $\mu$mol/L while that for the 2:1 bilirubin/albumin species was 0.0303 $\mu$mol/L. The results suggest that the albumin binding sites for bilirubin show positive cooperativity, as attempts to fit the curve to a fixed site model yielded one negative constant.

This assay shows that a single binding site on the free albumin is not present and that other binding methods measuring free albumin will not be accurate.

EXAMPLE 11

Change in Concentration of "a" (non-occupied bilirubin binding sites) During Oxidation:

Previous studies suggest that the velocity curve for the W & J method follows first order kinetics, implying that the oxidation products bind to albumin, i.e., the concentration of available albumin sites for binding bilirubin remain constant during the reaction. The concentration of unoccupied bilirubin binding sites would then remain essentially constant during the reaction. This was investigated further as it is important in validating the formulas used to calculate the UUBC.

A bilirubin–$^{14}$C/defatted albumin solution (molar ratio 0.42) containing 278 $\mu$mol/L bilirubin and 60,839 counts per minute, 50 $\mu$g/mL peroxidase, and 1000 $\mu$mol/L ethyl hydrogen peroxide were allowed to react for 8 minutes. At various times (0 to 8 minutes), 100 $\mu$l of reaction mix was removed and added to 10 $\mu$l of 100 mmol/L Na$_2$S to stop the reaction. The bilirubin concentration was calculated from the absorption at 460 nm after dilution to 1.0 ml with 0.055M Somensen's buffer, and the entire diluted reaction mixture was then placed on a Sephadex G25 0.5×5 cm (diameter×length) column prepared according to the manufacturer's instructions. The albumin fraction was then eluted with buffer. The bilirubin remaining and the radioactivity of the eluate were measured at each time interval to determine whether the oxidation products remained bound to albumin during the reaction and therefore passed through the Sephadex column with the albumin.

The results from the studies to determine whether the concentration of non-occupied bilirubin-albumin binding sites changed during the reaction are given in Table 4.

TABLE 4

Change in bilirubin concentration and Sephadex column radioactivity during bilirubin oxidation by peroxidase and peroxide (duplicates).

| Reaction Time (min) | Bilirubin ($\mu$mol/L) (% time 0) | Eluate counts/min (% time 0) |
|---|---|---|
| 0 | 4.86 (100%) | 57,675 (100%) |
| 0 | 4.93 (100%) | 57,692 (100%) |
| 4 | 3.07 (63%) | 55,797 (97%) |
| 4 | 3.36 (68%) | 53,070 (92%) |
| 6 | 2.70 (55%) | 50,119 (87%) |
| 6 | 2.60 (53%) | 47,500 (82%) |
| 8 | 2.14 (44%) | 50,174 (87%) |
| 8 | 2.24 (46%) | 49,405 (86%) |

Preliminary studies showed that about 5% of the radioactivity was removed from the sample by passing it through the column. While the total bilirubin concentration fell to about 46% of its original value by 8 minutes of reaction, 86% of the radioactivity remained with the albumin indicating that the oxidation products were still mostly bound to albumin.

This experiment shows that it is appropriate to consider the free albumin as a constant in the calculations hereinabove when about half of the bilirubin was oxidized.

The instant invention is shown and described herein in what is considered to be the most practical and preferred embodiments. It is recognized, however, that departures may be made from these embodiments which are within the scope of the invention and that modifications will occur to one of ordinary skill in the art upon reading this disclosure. Throughout this description, the preferred embodiment and examples shown should be considered as exemplars, rather than as limitations on the present invention. Accordingly, it is to be understood that the invention is not to be limited by the specific illustrated embodiments, but only by the scope of the appended claims.

What is claimed:

1. A process for determining the concentration of unbound, unconjugated bilirubin in a sample comprising:
   (a) determining the concentration of conjugated and unconjugated bilirubin in a first aliquot of said sample,
   (b) mixing a second aliquot of said sample with a bilirubin oxidizing reagent and a catalytically effective amount of a standardized catalyzing reagent, in which the first order rate constant for catalyzing the oxidation of bilirubin by said oxidizing reagent has been determined, under conditions effective to oxidize the unconjugated bilirubin for a predetermined amount of time sufficiently short so that the amount of bilirubin oxidized is less than about 50% of the total bilirubin concentration, said dilution of said second aliquot sample from the addition of the oxidizing reagent and the catalyzing reagent being less than about 3:1 by volume;
   (c) stopping the oxidation reaction at said predetermined time and determining the concentration of conjugated and unconjugated bilirubin remaining in said second aliquot after oxidation, and
   (d) determining the steady state unconjugated unbound bilirubin concentration, designated as $b_{ss}$, from the calculation of the following equation:

$$b_{ss} = -B_o \cdot \text{Log}(B_t/B_o)/(\text{dilution} \cdot K_p \cdot P \cdot t)$$

wherein $b_{ss}$ is the steady state unconjugated unbound bilirubin concentration;

$B_o$ is the unconjugated bilirubin concentration in said serum sample, its value determined in step (a);

$B_t$ is the unconjugated bilirubin concentration in said sample after oxidation of bilirubin by the oxidizing reagent in the presence of a standardized catalyzing reagent for a predetermined amount of time, its value determined in step (c);

dilution is the sample dilution resulting from the addition of oxidizing and catalyzing reagents;

t is the predetermined reaction time for the oxidation reaction;

P is the concentration of the standardized catalyzing reagent; and $K_p$ is the first order rate constant for the catalyzed oxidation of bilirubin by said oxidizing agent in the absence of albumin or other molecules capable of binding to bilirubin.

2. A process for determining the concentration of unbound, unconjugated bilirubin in a sample comprising:

(a) determining the concentration of unconjugated bilirubin ($B_o$) in said sample;

(b) mixing a second aliquot of said sample with a bilirubin oxidizing reagent, and a catalytically effective amount of a standardized catalyzing reagent, in which the first order rate constant for catalyzing the oxidation of bilirubin by said oxidizing reagent has been determined, under conditions effective to oxidize the unconjugated bilirubin for a predetermined amount of time sufficiently short so that the amount of bilirubin oxidized is less than about 50% of the total bilirubin concentration, said dilution of said aliquot sample from the addition of said oxidizing and catalyzing reagents being less than about 3:1 by volume;

(c) stopping the oxidation reaction at said predetermined time and determining the concentration of unoxidized conjugated and unconjugated bilirubin in said second aliquot sample ($B_t$);

(d) mixing a third aliquot of said sample of equal volume to that in step (b) with an oxidizing reagent and a buffer in the absence of any added catalyzing reagent for the same amount of time as in step (b), and determining the concentration of unoxidized unconjugated bilirubin in said third aliquot sample, whereby the amount of buffer added is equal in volume to the amount of catalyzing reagent added in step (b) and the volume and concentration of oxidizing reagent added is equal to that utilized in step (b); and (e) determining the steady state unconjugated non-albumin bound bilirubin concentration designated as $b_{ss}$ from the calculation of the following equation $$b_{ss} = -[B_o \cdot \text{Log}((B_o - B_b + B_t)/B_o)]/(\text{dilution} \cdot K_p \cdot P \cdot t)$$

wherein $b_{ss}$ is the steady state unconjugated non-albumin bound bilirubin concentration;

$B_o$ is the unconjugated bilirubin concentration in said serum sample, its value determined in step (a);

$B_t$ is the unconjugated bilirubin concentration in said serum sample after oxidation of bilirubin by the oxidizing reagent in the presence of a standardized catalyzing reagent for a predetermined amount of time, its value determined in step (c);

$B_b$ is the background oxidation in the absence of a standardized catalytic reagent;

dilution is the sample dilution resulting from the addition of oxidizing and catalyzing reagents;

t is the predetermined reaction time for the oxidation reaction;

P is the concentration of the standardized catalyzing reagent; and $K_p$ is the first order rate constant for the catalyzed oxidation of bilirubin by said oxidizing agent.

3. The process for determining the concentration of unbound unconjugated bilirubin in a sample comprising:

(a) determining the concentration of conjugated and unconjugated bilirubin in a first aliquot of said sample;

(b) mixing a second aliquot of said sample, with a bilirubin oxidizing reagent and a first catalytically effective amount of a standardized catalyzing reagent in which the first order rate constant for catalyzing the oxidation of bilirubin utilizing said oxidizing reagent has been determined, under conditions effective to oxidize the unconjugated bilirubin for a predetermined amount of time sufficiently short so that the amount of bilirubin oxidized is less than about 50% of the total bilirubin concentration, said dilution of said aliquot sample from the addition of said oxidizing and catalyzing reagents being less than about 3:1 by volume;

(c) stopping the oxidation reaction at said predetermined time and determining the concentration of unoxidized conjugated and unconjugated bilirubin in said second aliquot;

(d) repeating steps (b) and (c) with a second amount of the same catalyzing reagent in a third aliquot, said second amount of catalyzing reagent being different from the first amount of catalyzing reagent;

(e) mixing a fourth aliquot of said sample of equal volume to that in step (b) with an oxidizing reagent and a buffer in the absence of any added catalyzing reagent for the same amount of time as in step (b), and determining the concentration of unoxidized unconjugated bilirubin in said fourth aliquot, whereby the amount of buffer added is equal in volume to the amount of catalyzing reagent added in step (b) and the volume and concentration of oxidizing reagent added is equal to that utilized in step (b); and (f) determining the steady state unconjugated unbound concentration therefrom at the two catalyzing reagent concentrations, using the equations $$b_{ss1} = -[B_o \cdot \text{Log}((B_o - B_b + B_{t1})/B_o)]/(\text{dilution} \cdot K_p \cdot P_1 \cdot t_1)$$

$$b_{ss2} = -[B_o \cdot \text{Log}((B_o - B_b + B_{t2})/B_o)]/(\text{dilution} \cdot K_p \cdot P_2 \cdot t_2)$$

and, determining $k_{-1}$, $B_o$ and $k_1 \cdot$ a from the equations $$b_{ss1} = \frac{k_{-1} B_o}{(k_1 a) + (K_p \cdot P_1)} \quad b_{ss2} = \frac{k_{-1} B_o}{k_1 a + (K_p \cdot P_2)}$$

and then determining the equilibrium unbound unconjugated bilirubin $b_{eq}$ from the equation $$b_{eq} = \frac{k_{-1} \cdot B_o}{k_1 a}$$

wherein
$b_{ss1}$ is the 1st steady state unconjugated unbound albumin concentration at the first concentration of the catalyzing reagent;
$b_{ss2}$ is the 2nd steady state unconjugated unbound albumin concentration at the second concentration of the catalyzing reagent;
$P_1$ is the first catalyzing reagent concentration;
$P_2$ is the second catalyzing reagent concentration;
$B_o$ is the unconjugated bilirubin concentration in said serum sample, its value determined in step (a);
$B_b$ is the background oxidation in the absence of a standardized catalyst reagent;
$B_{t1}$ and $B_{t2}$ are the unconjugated bilirubin concentration, respectively in the sample, from step (c) and step (d) respectively after oxidation of the bilirubin by the oxidizing reagent in the presence of the catalyzing reagent for a predetermined amount of time;
dilution is the sample dilution resulting from the addition of oxidizing and catalyzing reagents;
$t_1$ and $t_2$ are independently predetermined reaction time for the oxidation reaction and $t_1$ and $t_2$ may be the same or different;
$K_p$ is the first order rate constant for the catalyzed oxidation of bilirubin by said oxidizing agent;
$k_{-1}$ is the rate constant of the dissociation of bilirubin from albumin;
$k_1$ is the rate association constant for albumin and bilirubin;
a is the concentration of unbound albumin; and
$b_{eq}$ is the equilibrium concentration of unbound unconjugated bilirubin.

4. The process for determining the concentration of unbound unconjugated bilirubin in a sample comprising:
(a) determining the concentration of conjugated and unconjugated bilirubin in a first aliquot of said sample;
(b) mixing a second aliquot of said sample with a bilirubin oxidizing reagent, and a first catalytically effective amount of a standardized catalyzing reagent in which the first order rate constant for catalyzing the oxidation of bilirubin utilizing said oxidizing reagent has been determined, under conditions effective to oxidize the unconjugated bilirubin for a predetermined amount of time sufficiently short so that the amount of bilirubin oxidized is less than about 50% of the total bilirubin concentration, said dilution of said aliquot sample from the addition of said oxidizing and catalyzing reagents being less than about 3:1 by volume;
(c) stopping the oxidation reaction at said predetermined time and determining the concentration of unoxidized conjugated and unconjugated bilirubin in said second aliquot;
(d) repeating steps (b) and (c) with a second amount of the same catalyzing reagent in a third aliquot, said second amount of catalyzing reagent being different from the first amount of catalyzing reagent;
(e) determining the steady state unconjugated unbound albumin concentration therefrom at the two catalyzing reagent concentrations, using the equations $b_{ss1} = -[B_o \cdot \text{Log} (B_{t1}/B_o)]/(\text{dilution} \cdot K_p \cdot P_1 \cdot t_1)$ $b_{ss2} = -[B_o \cdot \text{Log} (B_{t2}/B_o)]/(\text{dilution} \cdot K_p \cdot P_2 \cdot t_2)$ and, determining $k_{-1}$, $B_o$ and $k_1 \cdot a$ from the equations $$b_{ss1} = \frac{k_{-1} B_o}{(k_1 a) + (K_p \cdot P_1)} \quad b_{ss2} = \frac{k_{-1} B_o}{(k_1 a) + (K_p \cdot P_2)}$$

and then determining the equilibrium unbound unconjugated bilirubin $b_{eq}$ from the equation $$b_{eq} = \frac{k_{-1} \cdot B_o}{k_1 a},$$

wherein
$b_{ss1}$ is the 1st steady state unconjugated unbound albumin concentration at the first concentration of the catalyzing reagent;
$b_{ss2}$ is the 2nd steady state unconjugated unbound albumin concentration at the second concentration of the catalyzing reagent;
$P_1$ is the first catalyzing reagent concentration;
$P_2$ is the second catalyzing reagent concentration;
$B_o$ is the unconjugated bilirubin concentration in said serum sample, its value determined in step (a);
$B_b$ is the background oxidation in the absence of a standardized catalyst reagent;
$B_{t1}$ and $B_{t2}$ are the unconjugated bilirubin concentrations, respectively, in the sample from step (c) and step (d), respectively, after oxidation of the bilirubin by the oxidizing reagent in the presence of standardized catalyzing reagent for a predetermined amount of time;
dilution is the sample dilution resulting from the addition of oxidizing and catalyzing reagents;
$t_1$ and $t_2$ are independently the predetermined reaction times for the oxidation reactions and $t_1$ and $t_2$ may be the same or different;
$K_p$ is the first order rate constant for the catalyzed oxidation of bilirubin by said oxidizing agent;
$k_{-1}$ is the rate constant of the dissociation of bilirubin from albumin;
$k_1$ is the rate association constant for albumin and bilirubin;
a is the concentration of unbound albumin; and
b is the equilibrium concentration of unbound unconjugated bilirubin.

5. A process for determining the concentration of unbound, unconjugated bilirubin in a sample from a newborn, whose total bilirubin concentration is known, which comprises
(a) mixing an aliquot of said sample with a bilirubin oxidizing reagent and a catalytically effective amount of a standardized catalyzing reagent in which the first order rate constant for catalyzing the oxidation of bilirubin by said oxidizing reagent has been determined, under conditions effective to oxidize the unconjugated bilirubin for a predetermined amount of time sufficiently short so that the amount of bilirubin oxidized is less than about 50% of the total bilirubin concentration, said dilution of said sample from the addition of the oxidizing reagent and catalyzing reagent being less than about 3:1 by volume;
(b) stopping the oxidation reaction at said predetermined time and determining the concentration of conjugated bilirubin remaining in said aliquot after oxidization; and (c) determining the steady state unconjugated unbound bilirubin concentration, designated as $b_{ss}$ from the calculation of the following equation:

$$b_{ss} = -B_o \cdot \text{Log}(B_t/B_o)/(\text{dilution} \cdot K_p \cdot P \cdot t)$$

wherein $b_{ss}$ is the steady state unconjugated unbound bilirubin concentration;

$B_o$ is the unconjugated bilirubin concentration in said sample;

$B_t$ is the unconjugated bilirubin concentration in said sample after oxidation by bilirubin by the oxidizing reagent in the presence of a standardized catalyzing reagent for a predetermined amount of time; its value determined in step (b);

dilution is the sample dilution resulting from the addition of oxidizing and catalyzing reagents;

t is the predetermined reaction time for the oxidation reaction;

P is the concentration of the standardized catalyzing reagent; and $K_p$ is the first order rate constant for the catalyzed oxidation of bilirubin by said oxidizing agent in the absence of albumin or other molecules capable of binding to bilirubin.

6. The process according to claim 2 or 3 wherein $B_o - B_b$ is significantly less than $B_t$ and the value of $B_o - B_b$ relative to $B_t$ is approximated to be 0.

7. The process according to any one of claims 1–5 wherein the catalyzing reagent is peroxidase and the oxidizing reagent is peroxide.

8. The process according to claim 7 wherein the peroxidase is horseradish peroxidase.

9. The process according to any one of claims 1 to 4 wherein the concentration of conjugated and unconjugated bilirubin in said sample are determined as follows:

(a) mixing in a first container an aliquot of said serum sample and an effective amount of a diazo reagent for sufficient time to form a colored complex with the total amount of conjugated bilirubin in said sample, and measuring the concentration thereof;

(b) adding to the first container an accelerating effective amount of an accelerator and mixing said accelerator with the product of (a) for sufficient time to react with the unconjugated bilirubin to form a second colored complex and determining the concentration of conjugated and unconjugated bilirubin therefrom.

10. The process of determining the concentration of unbound, unconjugated bilirubin in a buffered serum sample according to claim 2 or 3 comprising:

(a) mixing in a first container an aliquot of said serum sample and an effective amount of a diazo reagent for sufficient time to form a colored complex with the total amount of conjugated bilirubin in said sample, and measuring the concentration thereof;

(b) adding to the first container an accelerating effective amount of an accelerator and mixing said accelerator with the product of (a) for sufficient time to react with the unconjugated bilirubin to form a second colored complex and determining the concentration thereof, denoted as $B_o$;

(c) adding to a second container a second aliquot sample, peroxide and a catalytically effective amount of a standardized peroxidase solution having a predetermined first order rate constant for peroxidase catalyzed oxidation of bilirubin by peroxide and mixing the same for a predetermined amount of time under conditions effective to oxidize the unconjugated bilirubin, said oxidized unconjugated bilirubin being less than about 50% of the total bilirubin concentration and the dilution of said second aliquot sample from the addition of peroxide and peroxidase being less than about 3:1 by volume;

(d) adding diazo reagent to the product of step (c) for sufficient time to form a colored complex with the total amount of conjugated bilirubin in said sample and measuring the concentration thereof;

(e) adding to the second container an accelerating effective amount of an accelerator and mixing with the product of step (d) for sufficient time to react with the remaining unconjugated bilirubin and determining therefrom the amount of unconjugated bilirubin that was oxidized, designated as $B_t$;

(f) mixing in a third container in the absence of any added peroxidase, additional buffer solution equal in volume to the amount of peroxidase solution added in step (c), and an aliquot sample of said serum plasma and peroxide, the volume of said serum sample and peroxide being the same as that utilized in step (c), and mixing the solution for the same amount of time as in step (c);

(g) adding to said third container the same amount of diazo reagent and the same amount of accelerator utilized in steps (d) and (e), respectively, and determining therefrom the amount of unoxidized unconjugated bilirubin present in said sample designated as $B_b$; and (h) determining the steady state unconjugated non-albumin bound bilirubin concentration.

11. The process according to claim 9 wherein the diazo reagent is formed by the reaction of an aromatic amine with nitrite in the presence of an acid.

12. The process according to claim 11 wherein the aromatic amine is sulfanilic acid.

13. The process according to claim 9 wherein the accelerator is methanol.

14. The process according to claim 5 wherein the concentration of unconjugated bilirubin in said sample is determined as follows:

adding to the sample an effective amount of accelerator and diazo reagent for sufficient time to react with the unoxidized unconjugated bilirubin to form a colored complex and determining the concentration of unconjugated bilirubin in said sample therefrom.

15. The process according to claim 14 wherein the diazo reagent is formed by the reaction of an aromatic amine with nitrite in the presence of an acid.

16. The process according to claim 15 wherein the aromatic amine is sulfanilic acid.

17. The process according to claim 14 wherein the accelerator is methanol.

18. The process according to any one of claims 1 to 5 wherein the concentration of the peroxidase ranges from about 1 to 150 $\mu$g/mL.

19. The process according to any one of claims 1 to 5 wherein the volume of sample present in the aliquot is equal to or greater than about 10 $\mu$L but less than about 100 $\mu$L.

20. The process according to any one of claims 1 to 5 wherein the sample is blood serum or plasma from a mammal.

21. The process according to claim 20 wherein the mammal is human.

* * * * *